(12) United States Patent
Zheng et al.

(10) Patent No.: US 8,716,275 B2
(45) Date of Patent: May 6, 2014

(54) COMPOUND FOR THE TREATMENT OF HEPATITIS C

(71) Applicant: Bristol-Meyers Squibb Company, Princeton, NJ (US)

(72) Inventors: Zhizhen Barbara Zheng, Cheshire, CT (US); Stanley D'Andrea, Wallingford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 13/651,538

(22) Filed: Oct. 15, 2012

(65) Prior Publication Data
US 2013/0102589 A1   Apr. 25, 2013

Related U.S. Application Data

(60) Provisional application No. 61/549,450, filed on Oct. 20, 2011.

(51) Int. Cl.
   *A01N 43/00*     (2006.01)
   *A61K 31/55*    (2006.01)
   *C07D 223/14*   (2006.01)

(52) U.S. Cl.
   USPC .................................... 514/214.01; 540/576

(58) Field of Classification Search
   None
   See application file for complete search history.

(56) References Cited

U.S. PATENT DOCUMENTS 8,129,367 B2 *   3/2012   Hewawasam et al. ... 514/214.01
2009/0130057 A1 *   5/2009   Hewawasam et al. ....... 424/85.2

* cited by examiner

*Primary Examiner* — Craig Ricci
*Assistant Examiner* — Jared D Barsky
(74) *Attorney, Agent, or Firm* — James Epperson

(57) ABSTRACT

The present invention provides (1aR,12bS)-8-cyclohexyl-11-fluoro-N-((1-methylcyclopropyl)sulfonyl)-1a-((3-methyl-3,8-diazabicyclo[3.2.1]oct-8-yl)carbonyl)-1,1a,2,12b-tetrahydrocyclopropa[d]indolo[2,1-a][2]benzazepine-5-carboxamide (formula I), including pharmaceutically acceptable salts, as well as compositions and methods of using the compound. The compound has activity against hepatitis C virus (HCV) and may be useful in treating those infected with HCV.

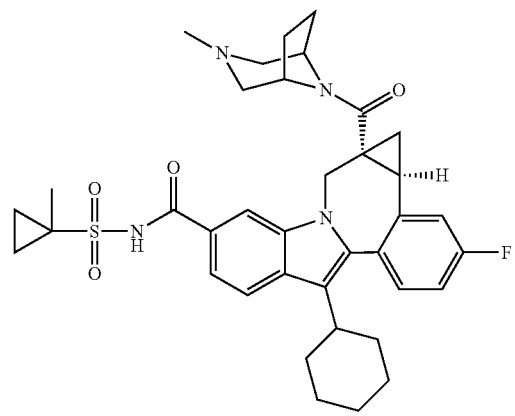

3 Claims, No Drawings

COMPOUND FOR THE TREATMENT OF HEPATITIS C

CROSS-REFERENCE TO RELATED APPLICATIONS

This application claims the benefit of U.S. provisional application Ser. No. 61/549,450 filed Oct. 20, 2011.

BACKGROUND OF THE INVENTION

The disclosure relates to (1aR,12bS)-8-cyclohexyl-11-fluoro-N-((1-methylcyclopropyl)sulfonyl)-1a-((3-methyl-3,8-diazabicyclo[3.2.1]oct-8-yl)carbonyl)-1,1a,2,12b-tetrahydrocyclopropa[d]indolo[2,1-a][2]benzazepine-5-carboxamide (Compound 1, formula I), including pharmaceutically acceptable salts, as well as compositions and methods of using the compound. The compound has activity against hepatitis C virus (HCV) and may be useful in treating those infected with HCV.

Hepatitis C virus (HCV) is a major human pathogen, infecting an estimated 170 million persons worldwide. Hepatitis C virus (HCV) is the most common bloodborne infection in the USA and worldwide and is the leading cause of liver transplantation (Eric Chak et.al. *Liver International* 2011, 1090-1101) A substantial fraction of these HCV infected individuals develop serious progressive liver disease, including cirrhosis and hepatocellular carcinoma (Lauer, G. M.; Walker, B. D. *N. Engl. J. Med.* 2001, 345, 41-52).

HCV is a positive-stranded RNA virus. Considerable heterogeneity is found within the nucleotide and encoded amino acid sequence throughout the HCV genome. At least six major genotypes have been characterized, and more than 50 subtypes have been described adding to the need for new therapies.

The genome consists of approximately 9500 nucleotides and has a single open reading frame (ORF) encoding a single large polyprotein of about 3000 amino acids. In infected cells, this polyprotein is cleaved at multiple sites by cellular and viral proteases to produce the structural and non-structural (NS) proteins. The NS proteins (NS3, NS4A, NS4B, NS5A, and NS5B) are required for viral RNA replication. NS3 is a serine protease that mediates cleavage of the polyprotein. The NS4A protein is a cofactor for the NS3 protease. The complex formation of the NS3 protein with NS4A seems necessary to the processing events, enhancing the proteolytic efficiency at all of the sites. The NS3 protein also exhibits nucleoside triphosphatase and RNA helicase activities. NS5B (also referred to as HCV polymerase) is a RNA-dependent RNA polymerase that is involved in the replication of HCV. The NS5B RNA-dependent RNA polymerase (RdRp) is essential to the replication cycle of HCV (Tomei L, Altamura S, Paonessa G, et al. *Antivir Chem Chemother* 2005, 16, 225-245). The HCV NS5B protein is described in "Structural Analysis of the Hepatitis C Virus RNA Polymerase in Complex with Ribonucleotides (Bressanelli; S. et al., *Journal of Virology* 2002, 3482-3492; and Defrancesco and Rice, *Clinics in Liver Disease* 2003, 7, 211-242. The NS5B crystal structure reveals a typical right-handed polymerase containing thumb, palm and finger domains surrounding the active site. (Lesburg C. A., Cable, M. B., Ferrari, et al. *Nat Struc Biol* 1999, 6, 937-943.) NS5B is the catalytic enzyme responsible for RNA replication and participates in higher order complexes at intracellular lipid membranes in association with various viral proteins and nucleic acids as well as host proteins. (El Hage N and Luo G. *J Gen Virol* 2003, 84, 2761-2769. Gao L, Aizaki H, He J W, et al. *J Virol* 2004, 78, 3480-3488) Examples of NS5B protein-protein interactions include binding to the NS3 helicase domain, facilitating RNA unwinding, and binding to the NS5A protein, a regulator of viral replication. (Jennings, et al. *Biochemistry* 2008, 47, 1126-1135. McCormick C J, Brown D, Griffin S, et al. *J Gen Virol* 2006, 87(Pt 1), 93-102).

HCV NS5B polymerase inhibitors can be divided into two classes based on their mode of inhibition: nucleoside (NUC) inhibitors compete with natural substrates and non-nucleoside inhibitors (NNI) are non-competitive allosteric inhibitors. Both NUC inhibitors and NNI have clinical proof of principal of antiviral activity via inhibition of the NS5B target (Gelman, M A. and J S. Glenn (2011) Mixing the right hepatitis C inhibitor cocktail. Trends in Molecular Medicine 17:1, 34-46; Soriano V., E. Vispo, E. Poveda, P. Labarga, L. Martin-Carbonero, J V. Fernandez-Montero and P. Barreiro (2011) Directly acting antivirals against hepatitis C virus. J Antimicrob Chemother 66, 1673-1686). NNI prevent conformational transitions of the polymerase that are required for the initiation of RNA synthesis (Ma H., V. Leveque, A. De Witte, W. Li, T. Hendricks, S M. Clausen, N. Cammack, K. Klumpp. (2005) Inhibition of native hepatitis C virus replicase by nucleotide and non-nucleoside inhibitors. Virology 332, 8-15). Co-crystals of NNI show that they bind to one of at least three distinct sites on the polymerase, consistent with the diverse patterns of resistance observed for these inhibitors in vitro and in vivo (Beaulieu, P. (2009) Recent advances in the development of NS5B polymerase inhibitors for the treatment of hepatitis C virus infection. Expert Opinion on Therapeutic Patents. 19, 145-64). These studies substantiate observations in the HCV RNA replicon system in which inhibition of NS5B blocks viral replication. (Tomei L, Altamura S, Paonessa G, et al. *Antivir Chem Chemother* 2005, 16, 225-245).

Previously, the most effective HCV therapy employed a combination of alpha-interferon and ribavirin, leading to sustained efficacy in only 40% of genotype 1 patients (Poynard, T. et al. *Lancet* 1998, 352, 1426-1432). Clinical results demonstrate that pegylated alpha-interferon is superior to unmodified alpha-interferon as monotherapy (Zeuzem, S. et al. *N. Engl. J. Med.* 2000, 343, 1666-1672). However, even with experimental therapeutic regimens involving combinations of pegylated alpha-interferon and ribavirin, a substantial fraction of patients did not have a sustained reduction in viral load. In 2011, improved therapies for genotype 1 patients that include an HCV NS3 protease inhibitor, a small molecule direct acting antiviral (DAA), plus interferon and ribavirin were approved by FDA. Two protease inhibitors (IN-CIVEK™ (Telaprevir) and VICTRELIS™ (Boceprevir) were approved; thus a choice of drug exists for combination therapy with interferon and ribavirin. (Ghany, M G., D R. Nelson, D B. Strader, D L. Thomas, and L B. Seeff. (2011) An Update on Treatment of Genotype 1 Chronic Hepatitis C Virus Infection: 2011 Practice Guideline by the American Association for the Study of Liver Diseases. Hepatology, 54(4): 1433-1444).

Currently, significant research efforts are focused on further improvement of cure rates, by improving tolerability, addressing the needs of patients whose virus or genetic markers make their disease less responsive to interferon based therapy, and shortening duration of therapy. Interferons with fewer side effects and interferon free regimens of small molecule DAA combinations are being tested. Because of the rapid replication rate and development of resistance by HCV, it is believed that treatment regimens will necessarily be combinations of agents.

Hepatitis C infected patients typically have a long (>10 years) asymptomatic phase of disease that occurs before substantial hepatic injury and symptoms are manifested. For this reasons, HCV infected individuals initially maintain a high quality of life or may not even know they are infected. Since all currently approved treatments include interferon and ribavirin which are associated with serious side effects, and since the recently approved protease inhibitors are associated with additional side effects (rash and anemia), many HCV infected patients choose to delay therapy until more acceptable regimens, expected within this decade, are approved. In the future, agents that have actual or perceived serious liabilities, such as risk for causing cardiovascular events or severe hepatotoxicity, will not be widely utilized for therapy. Thus, current research is focused on the development of safe and effective inhibitor combinations that can deliver a cure for HCV infection in the absence of interferon. Considerable efforts aimed at identifying direct acting antiviral agents which inhibit Hepatitis C virus replication have been disclosed in the art. (Gelman, M A. and J S. Glenn (2011) Mixing the right hepatitis C inhibitor cocktail. Trends in Molecular Medicine 17:1, 34-46; Soriano V., E. Vispo, E. Poveda, P. Labarga, L. Martin-Carbonero, J V. Fernandez-Montero and P. Barreiro (2011) Directly acting antivirals against hepatitis C virus. J Antimicrob Chemother 66, 1673-1686.

The general methodology used by pharmaceutical companies to identify compounds that have the potential to be used in the treatment of HCV in human patients is similar to the methodology applied to other drug discovery targets. Initial assessment of potency vs. the therapeutic target (in this case the NS5B enzyme targeted for inhibition of hepatitis C) is done with enzyme and cell based assays. Compounds with acceptable potency are profiled in additional in vitro assays to assess their suitability for achieving good pharmacokinetic (PK) profiles in animal models (rodent or higher species). Examples are (i) in vitro assays to assess metabolic stability in the presence of microsomal membranes prepared from liver cells of human and other species, and (ii) permeability assay systems such as Caco-2 or PAMPA to assess the potential for absorption. In vitro assays such as general cytotoxicity and cytochrome P450 enzyme inhibition (indicates the potential for drug-drug interactions) are also used to assess potential safety liabilities.

One serious liability which all drug discovery programs have developed in vitro strategies to avoid is the prolongation of myocardial repolarization and lengthening the QT interval on the electrocardiogram, as these properties have been associated with an increased risk for the development of life-threatening ventricular arrhythmias and death. Compounds with this liability would obviously not be useful for the treatment of Hepatitis C. In almost every case, drugs that increase the QT interval also block a specific potassium channel [human Ether-a-go-go Related Gene (hERG)] in in vitro assays. The prolongation of repolarization is of particular importance because it has been associated with an increased risk for the subsequent development of malignant ventricular arrhythmias and death. In the presence of prolonged myocardial repolarization, some individuals may develop a distinct form of ventricular tachycardia known as torsades de pointes. The development of such drug related new or worsened ventricular arrhythmias is termed proarrhythmia. Routine in vitro assays include hERG potassium ion channel assays (in silico, high-throughput flux and patch-clamp electrophysiology) and a Purkinje fiber action potential assay. The hERG screens will identify compounds that likely will affect the cardiac rapidly activating delayed rectifier potassium current (IKr). Most drugs that prolong cardiac repolarization do so by blocking this current.

For compounds in clinical development where therapeutic exposures are known, experts have estimated that a margin of 30-fold or greater between hERG $IC_{50}$ and the therapeutic Cmax of compound not bound to protein could be sufficient for safety from hERG-mediated arrhythmias associated with QTc prolongation; although Redfern et al. suggest that increasing the margin even further would be prudent. (Redfern, W. S.; Carlsson, L.; Davis, A. S.; Lynch, W. G.; MacKenzie, I.; Palethorpe, S.; Siegl, P. K. S.; Strang, I.; Sullivan, A. T.; Wallis, R.; Camm, A. J.; Hammond, T. G. Relationships between preclinical cardiac electrophysiology, clinical QT interval prolongation and torsade de pointes for a broad range of drugs: evidence for a provisional safety margin in drug development. Cardiovascular Research (2003), 58(1), 32-45. De Bruin, M. L.; Pettersson, M.; Meyboom, R. H. B.; Hoes, A. W.; Leufkens, H. G. M. Anti-HERG activity and the risk of drug-induced arrhythmias and sudden death. European Heart Journal (2005), 26(6), 590-597). For the assessment of risk in preclinical programs, some guidelines have been developed by ICH (International Conference On Harmonisation Of Technical Requirements For Registration Of Pharmaceuticals For Human Use), and these are also provided on the FDA web site for guidance to industry. An excerpt of a pertinent section (2.2) on profiling preclinical compounds follows: 2.2. ICH S7B strategy: The chemical class of drug candidates determines the preclinical safety strategy. The golden standard for the in vitro IKr assay is the test for HERG interaction by means of patch-clamp studies. The in vivo telemetry assay allows the study of QT interval with integrated risk assessment. For in vitro cardiac action potential duration (APD) studies multicellular preparation from animal heart is needed to study potential adverse effects of drug candidates on the whole concert of cardiac voltage-gated ion channels.

For in vitro assessment the gold standard (patch clamp assay) is also used to meet FDA regulatory recommendations (hERG assay); however, this assay is low through-put and in silico and high-throughput flux (flipr) assays are used for initial screening of greater numbers of compounds. Flux results (flipr) are validated with the patch clamp assay.

Because in vivo assessments such as telemetry in animals are so labor intensive and costly, they are employed exclusively for compounds of interest with respect to the entire compound profile. These are compounds for which in vitro assays suggest there is a high likelihood they could continue to advance if profiled further. Alternatively, compounds used to provide a benchmark to validate in vitro assays may be assessed in vivo. This holds true for advanced in vitro APD studies as well. Purkinje fiber testing is also low-throughput and complements the hERG assay by assessing all of the major ionic currents which contribute to the cardiac action potential. Signals for effects on other cardiac ionic currents can be detected in this action potential assay and followed-up in patch-clamp studies on candidate cardiac ion channels (e.g. Na, Ca or other K channels such as Iks).

A number of compounds which are inhibitors of HCV NS5B are in clinical development or have advanced to clinical studies and been discontinued for various reasons. More specific to this application, HCV NS5B inhibitors which bind to a site referred to in the art as Site 1 have been disclosed in U.S. Pat. Nos. 7,399,758, 7,485,633 and published U.S. patent application 2009130057.

The novel compound of the present invention which falls within the definition of Formula I in US application publication 2009130057 is not disclosed or described in that application. Surprisingly, it has been discovered that (2R)-2-[[(4-chlorophenyl)sulfonyl][[2-fluoro-4-(1,2,4-oxadiazol-3-yl)phenyl]methyl]amino]-5,5,5-trifluoropentanamide possesses unique attributes which make it useful for the treatment of hepatitis C.

DESCRIPTION OF THE INVENTION

The present invention relates to (1aR,12bS)-8-cyclohexyl-11-fluoro-N-((1-methylcyclopropyl)sulfonyl)-1a-((3-methyl-3,8-diazabicyclo[3.2.1]oct-8-yl)carbonyl)-1,1a,2,12b-tetrahydrocyclopropa[d]indolo[2,1-a][2]benzazepine-5-carboxamide having the Formula I, its pharmaceutical formulations, and its use in treating hepatitis C.

I

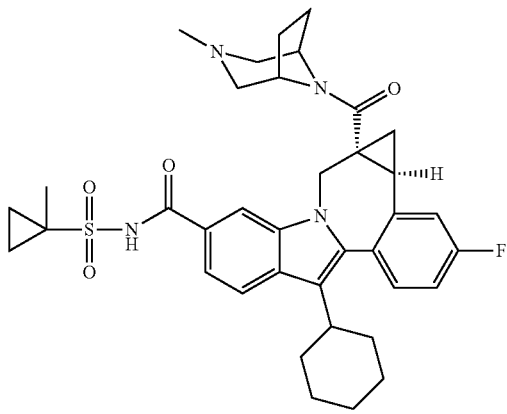

One aspect of the invention is the compound (1aR,12bS)-8-cyclohexyl-11-fluoro-N-((1-methylcyclopropyl)sulfonyl)-1a-((3-methyl-3,8-diazabicyclo[3.2.1]oct-8-yl)carbonyl)-1,1a,2,12b-tetrahydrocyclopropa[d]indolo[2,1-a][2]benzazepine-5-carboxamide, or a pharmaceutically acceptable salt thereof.

I

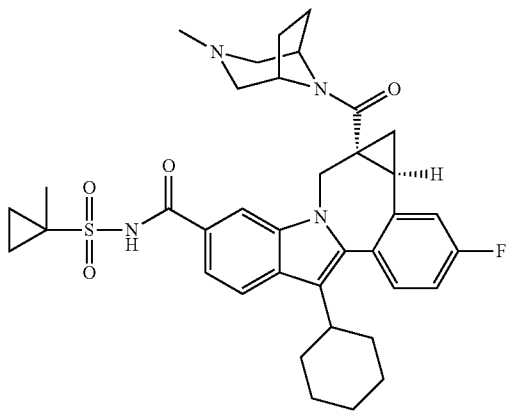

Another aspect of the invention is a pharmaceutical composition comprising a therapeutically effective amount of (1aR,12bS)-8-cyclohexyl-11-fluoro-N-((1-methylcyclopropyl)sulfonyl)-1a-((3-methyl-3,8-diazabicyclo[3.2.1]oct-8-yl)carbonyl)-1,1a,2,12b-tetrahydrocyclopropa[d]indolo[2,1-a][2]benzazepine-5-carboxamide, or a pharmaceutically acceptable salt thereof, and a pharmaceutically acceptable adjuvant, carrier or diluent.

Another aspect of the invention is a composition comprising a therapeutically effective amount of (1aR,12bS)-8-cyclohexyl-11-fluoro-N-((1-methylcyclopropyl)sulfonyl)-1a-((3-methyl-3,8-diazabicyclo[3.2.1]oct-8-yl)carbonyl)-1,1a,2,12b-tetrahydrocyclopropa[d]indolo[2,1-a][2]benzazepine-5-carboxamide and a compound having anti-HCV activity.

Another aspect of the invention is a composition comprising a therapeutically effective amount of (1aR,12bS)-8-cyclohexyl-11-fluoro-N-((1-methylcyclopropyl)sulfonyl)-1a-((3-methyl-3,8-diazabicyclo[3.2.1]oct-8-yl)carbonyl)-1,1a,2,12b-tetrahydrocyclopropa[d]indolo[2,1-a][2]benzazepine-5-carboxamide where the compound having anti-HCV activity is an interferon. Another aspect of the invention is where the interferon is selected from interferon alpha 2B, pegylated interferon alpha, consensus interferon, interferon alpha 2A, and lymphoblastoid interferon tau.

Another aspect of the invention is a composition comprising a therapeutically effective amount of (1aR,12bS)-8-cyclohexyl-11-fluoro-N-((1-methylcyclopropyl)sulfonyl)-1a-((3-methyl-3,8-diazabicyclo[3.2.1]oct-8-yl)carbonyl)-1,1a,2,12b-tetrahydrocyclopropa[d]indolo[2,1-a][2]benzazepine-5-carboxamide where the compound having anti-HCV activity is a cyclosporin. Another aspect of the invention is where the cyclosporin is cyclosporin A.

Another aspect of the invention is a composition comprising a therapeutically effective amount of (1aR,12bS)-8-cyclohexyl-11-fluoro-N-((1-methylcyclopropyl)sulfonyl)-1a-((3-methyl-3,8-diazabicyclo[3.2.1]oct-8-yl)carbonyl)-1,1a,2,12b-tetrahydrocyclopropa[d]indolo[2,1-a][2]benzazepine-5-carboxamide where the compound having anti-HCV activity is selected from the group consisting of interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is a composition comprising a therapeutically effective amount of (1aR,12bS)-8-cyclohexyl-11-fluoro-N-((1-methylcyclopropyl)sulfonyl)-1a-((3-methyl-3,8-diazabicyclo[3.2.1]oct-8-yl)carbonyl)-1,1a,2,12b-tetrahydrocyclopropa[d]indolo[2,1-a][2]benzazepine-5-carboxamide where the compound having anti-HCV activity is effective to inhibit the function of a target selected from HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is a composition comprising a therapeutically effective amount of (1aR,12bS)-8-cyclohexyl-11-fluoro-N-((1-methylcyclopropyl)sulfonyl)-1a-((3-methyl-3,8-diazabicyclo[3.2.1]oct-8-yl)carbonyl)-1,1a,2,12b-tetrahydrocyclopropa[d]indolo[2,1-a][2]benzazepine-5-carboxamide, or a pharmaceutically acceptable salt thereof, a pharmaceutically acceptable carrier, an interferon and ribavirin.

Another aspect of the invention is a method of treating an HCV infection in a patient comprising administering to the patient a therapeutically effective amount of 1aR,12bS)-8-cyclohexyl-11-fluoro-N-((1-methylcyclopropyl)sulfonyl)-1a-((3-methyl-3,8-diazabicyclo[3.2.1]oct-8-yl)carbonyl)-1,1a,2,12b-tetrahydrocyclopropa[d]indolo[2,1-a][2]benzazepine-5-carboxamide, or a pharmaceutically acceptable salt thereof. In another embodiment the compound is effective to inhibit the function of the HCV replicon. In another embodiment the compound is effective to inhibit the function of the HCV NS5B protein.

Another aspect of the invention is a method of treating an HCV infection in a patient comprising administering to the patient a therapeutically effective amount of a compound, or a 1aR,12bS)-8-cyclohexyl-11-fluoro-N-((1-methylcyclopropyl)sulfonyl)-1a-((3-methyl-3,8-diazabicyclo[3.2.1]oct-8-yl)carbonyl)-1,1a,2,12b-tetrahydrocyclopropa[d]indolo[2,1-a][2]benzazepine-5-carboxamide, in conjunction with (prior to, after, or concurrently) another compound having anti-HCV activity. Another aspect of the invention is the method where the other compound having anti-HCV activity is an interferon. Another aspect of the invention is the method where the interferon is selected from interferon alpha 2B, pegylated interferon alpha, consensus interferon, interferon alpha 2A, and lymphoblastoid interferon tau. Another aspect of the invention is the method where the other compound having anti-HCV activity is a cyclosporin. Another aspect of the invention is the method where the cyclosporin is cyclosporin A. Another aspect of the invention is the method where the other compound having anti-HCV activity is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine. Another aspect of the invention is the method where the other compound having anti-HCV activity is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection. Another aspect of the invention is the method where the other compound having anti-HCV activity is effective to inhibit the function of target in the HCV life cycle other than the HCV NS5B protein.

The invention includes all pharmaceutically acceptable salt forms of the compound. Pharmaceutically acceptable salts are those in which the counter ions do not contribute significantly to the physiological activity or toxicity of the compounds and, as such, function as pharmacological equivalents. These salts can be made according to common organic techniques employing commercially available reagents. Some anionic salt forms include acetate, acistrate, besylate, bromide, camsylate, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

As the compound of the present invention possesses asymmetric carbon atoms, the present invention includes stereoisomeric forms of the compound of Formula I. The use of a single designation such as (R) or (S) is intended to include mostly one stereoisomer. Mixtures of isomers can be separated into individual isomers according to known methods, e.g. fractional crystallization, adsorption chromatography or other suitable separation processes. Resulting racemates can be separated into antipodes in the usual manner after introduction of suitable salt-forming groupings, e.g. by forming a mixture of diastereosiomeric salts with optically active salt-forming agents, separating the mixture into diastereomeric salts and converting the separated salts into the free compounds. The enantiomeric forms may also be separated by fractionation through chiral high pressure liquid chromatography columns.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

"Therapeutically effective" means the amount of agent required to provide a meaningful patient benefit as understood by practitioners in the field of hepatitis and HCV infection.

"Patient" means a person infected with the HCV virus and suitable for therapy as understood by practitioners in the field of hepatitis and HCV infection.

"Treatment," "therapy," "regimen," "HCV infection," and related terms are used as understood by practitioners in the field of hepatitis and HCV infection.

The above therapeutic agents, when employed in combination with the compound of the present invention, may be used, for example, in those amounts indicated in the Physician's Desk Reference (PDR), where applicable or as otherwise determined by one of ordinary skill in the art. However, it will be understood that the amount of the compound actually administered will be determined by a physician, in the light of the relevant circumstances including the condition to be treated, the choice of compound to be administered, the chosen route of administration, the age, weight, and response of the individual patient, and the severity of the patient's symptoms.

For therapeutic use, the pharmacologically active compound of Formula I will normally be administered as a pharmaceutical composition comprising as the (or an) essential active ingredient at least one such compound in association with a solid or liquid pharmaceutically acceptable carrier and, optionally, with pharmaceutically acceptable adjuvants and excipients employing standard and conventional techniques.

The pharmaceutical compositions include suitable dosage forms for oral, parenteral (including subcutaneous, intramuscular, intradermal and intravenous), transdermal, sublingual, bronchial or nasal administration. Thus, if a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. Oral preparations include push-fit capsules made of gelatin, as well as soft, scaled capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in which case conventional suspending agents may be employed. Conventional preservatives, buffering agents and the like also may be added to the parenteral dosage forms. For topical or nasal administration, penetrants or permeation agents that are appropriate to the particular barrier to be permeated are used in the formulation. Such penetrants are known in the art. The pharmaceutical compositions are prepared by conventional techniques appropriate to the desired preparation containing appropriate amounts of the active ingredient, that is, the compound of Formula I according to the invention. See, for example, *Remington's Pharmaceutical Sciences*, Mack Publishing Company, Easton, Pa., 17th edition, 1985.

The invention also encompasses methods where the compound is given in combination therapy. That is, the compound can be used in conjunction with, but separately from, other agents useful in treating hepatitis and HCV infection. In these combination methods, the compound will generally be given in a daily dose of 1-100 mg/kg body weight in conjunction with other agents. The other agents generally will be given in the amounts used therapeutically. The specific dosing regime, however, will be determined by a physician using sound medical judgement.

Some examples of compounds suitable for compositions and methods are listed in Table 1.

TABLE 1

| Brand Name | Physiological Class | Type of Inhibitor or Target | Source Company |
| --- | --- | --- | --- |
| NIM811 | | Cyclophilin Inhibitor | Novartis |
| Zadaxin | | Immuno-modulator | Sciclone |
| Suvus | | Methylene blue | Bioenvision |
| Actilon (CPG10101) | | TLR9 agonist | Coley |
| Batabulin (T67) | Anticancer | β-tubulin inhibitor | Tularik Inc., South San Francisco, CA |
| ISIS 14803 | Antiviral | antisense | ISIS Pharmaceuticals Inc, Carlsbad, CA/Elan Phamaceuticals Inc., New York, NY |
| Summetrel | Antiviral | antiviral | Endo Pharmaceuticals Holdings Inc., Chadds Ford, PA |
| GS-9132 (ACH-806) | Antiviral | HCV Inhibitor | Achillion/Gilead |
| Pyrazolopyrimidine compounds and salts From WO-2005047288 26 May 2005 | Antiviral | HCV Inhibitors | Arrow Therapeutics Ltd. |
| Levovirin | Antiviral | IMPDH inhibitor | Ribapharm Inc., Costa Mesa, CA |
| Merimepodib (VX-497) | Antiviral | IMPDH inhibitor | Vertex Pharmaceuticals Inc., Cambridge, MA |
| XTL-6865 (XTL-002) | Antiviral | monoclonal antibody | XTL Biopharmaceuticals Ltd., Rehovot, Isreal |
| Telaprevir (VX-950, LY-570310) | Antiviral | NS3 serine protease inhibitor | Vertex Pharmaceuticals Inc., Cambridge, MA/Eli Lilly and Co. Inc., Indianapolis, IN |
| HCV-796 | Antiviral | NS5B Replicase Inhibitor | Wyeth/ Viropharma |
| NM-283 | Antiviral | NS5B Replicase Inhibitor | Idenix/Novartis |
| GL-59728 | Antiviral | NS5B Replicase Inhibitor | Gene Labs/ Novartis |
| GL-60667 | Antiviral | NS5B Replicase Inhibitor | Gene Labs/ Novartis |
| 2'C MeA | Antiviral | NS5B Replicase Inhibitor | Gilead |
| PSI 6130 | Antiviral | NS5B Replicase Inhibitor | Roche |

TABLE 1-continued

| Brand Name | Physiological Class | Type of Inhibitor or Target | Source Company |
|---|---|---|---|
| R1626 | Antiviral | NS5B Replicase Inhibitor | Roche |
| 2'C Methyl adenosine | Antiviral | NS5B Replicase Inhibitor | Merck |
| JTK-003 | Antiviral | RdRp inhibitor | Japan Tobacco Inc., Tokyo, Japan |
| Levovirin | Antiviral | ribavirin | ICN Pharmaceuticals, Costa Mesa, CA |
| Ribavirin | Antiviral | ribavirin | Schering-Plough Corporation, Kenilworth, NJ |
| Viramidine | Antiviral | Ribavirin Prodrug | Ribapharm Inc., Costa Mesa, CA |
| Heptazyme | Antiviral | ribozyme | Ribozyme Pharmaceuticals Inc., Boulder, CO |
| BILN-2061 | Antiviral | serine protease inhibitor | Boehringer Ingelheim Pharma KG, Ingelheim, Germany |
| SCH 503034 | Antiviral | serine protease inhibitor | Schering Plough |
| Zadazim | Immune modulator | Immune modulator | SciClone Pharmaceuticals Inc., San Mateo, CA |
| Ceplene | Immunomodulator | immune modulator | Maxim Pharmaceuticals Inc., San Diego, CA |
| CellCept | Immunosuppressant | HCV IgG immuno-suppressant | F. Hoffmann-La Roche LTD, Basel, Switzerland |
| Civacir | Immunosuppressant | HCV IgG immuno-suppressant | Nabi Biopharmaceuticals Inc., Boca Raton, FL |
| Albuferon-α | Interferon | albumin IFN-α2b | Human Genome Sciences Inc., Rockville, MD |
| Infergen A | Interferon | IFN alfacon-1 | InterMune Pharmaceuticals Inc., Brisbane, CA |
| Omega IFN | Interferon | IFN-ω | Intarcia Therapeutics |
| IFN-β and EMZ701 | Interferon | IFN-β and EMZ701 | Transition Therapeutics Inc., Ontario, Canada |
| Rebif | Interferon | IFN-β1a | Serono, Geneva, Switzerland |
| Roferon A | Interferon | IFN-α2a | F. Hoffmann-La Roche LTD, Basel, Switzerland |
| Intron A | Interferon | IFN-α2b | Schering-Plough Corporation, Kenilworth, NJ |
| Intron A and Zadaxin | Interferon | IFN-α2b/α1-thymosin | RegeneRx Biopharma. Inc., Bethesda, MD/ SciClone Pharmaceuticals Inc, San Mateo, CA |
| Rebetron | Interferon | IFN-α2b/ribavirin | Schering-Plough Corporation, Kenilworth, NJ |
| Actimmune | Interferon | INF-γ | InterMune Inc., Brisbane, CA |
| Interferon-β | Interferon | Interferon-β-1a | Serono |
| Multiferon | Interferon | Long lasting IFN | Viragen/ Valentis |

TABLE 1-continued

| Brand Name | Physiological Class | Type of Inhibitor or Target | Source Company |
|---|---|---|---|
| Wellferon | Interferon | Lympho-blastoid IFN-αn1 | GlaxoSmithKline plc, Uxbridge, UK |
| Omniferon | Interferon | natural IFN-α | Viragen Inc., Plantation, FL |
| Pegasys | Interferon | PEGylated IFN-α2a | F. Hoffmann-La Roche LTD, Basel, Switzerland |
| Pegasys and Ceplene | Interferon | PEGylated IFN-α2a/ immune modulator | Maxim Pharmaceuticals Inc., San Diego, CA |
| Pegasys and Ribavirin | Interferon | PEGylated IFN-α2a/ribavirin | F. Hoffmann-La Roche LTD, Basel, Switzerland |
| PEG-Intron | Interferon | PEGylated IFN-α2b | Schering-Plough Corporation, Kenilworth, NJ |
| PEG-Intron/ Ribavirin | Interferon | PEGylated IFN-α2b/ribavirin | Schering-Plough Corporation, Kenilworth, NJ |
| IP-501 | Liver protection | antifibrotic | Indevus Pharmaceuticals Inc., Lexington, MA |
| IDN-6556 | Liver protection | caspase inhibitor | Idun Pharmaceuticals Inc., San Diego, CA |
| ITMN-191 (R-7227) | Antiviral | serine protease inhibitor | InterMune Pharmaceuticals Inc., Brisbane, CA |
| GL-59728 | Antiviral | NS5B Replicase Inhibitor | Genelabs |
| ANA-971 | Antiviral | TLR-7 agonist | Anadys |
| Boceprevir | Antiviral | serine protease inhibitor | Schering Plough |
| TMS-435 | Antiviral | serine protease inhibitor | Tibotec BVBA, Mechelen, Belgium |
| BI-201335 | Antiviral | serine protease inhibitor | Boehringer Ingelheim Pharma KG, Ingelheim, Germany |
| MK-7009 | Antiviral | serine protease inhibitor | Merck |
| PF-00868554 | Antiviral | replicase inhibitor | Pfizer |
| ANA598 | Antiviral | Non-Nucleoside NS5B Polymerase Inhibitor | Anadys Pharmaceuticals, Inc., San Diego, CA, USA |
| IDX375 | Antiviral | Non-Nucleoside Replicase Inhibitor | Idenix Pharmaceuticals, Cambridge, MA, USA |
| BILB 1941 | Antiviral | NS5B Polymerase Inhibitor | Boehringer Ingelheim Canada Ltd R&D, Laval, QC, Canada |
| PSI-7851 | Antiviral | Nucleoside Polymerase Inhibitor | Pharmasset, Princeton, NJ, USA |
| PSI-7977 | Antiviral | Nucleotide NS5B Polymerase Inhibitor | Pharmasset, Princeton, NJ, USA |
| VCH-759 | Antiviral | NS5B Polymerase Inhibitor | ViroChem Pharma |
| VCH-916 | Antiviral | NS5B Polymerase Inhibitor | ViroChem Pharma |
| GS-9190 | Antiviral | NS5B Polymerase Inhibitor | Gilead |

TABLE 1-continued

| Brand Name | Physiological Class | Type of Inhibitor or Target | Source Company |
|---|---|---|---|
| Peg-interferon lamda | Antiviral | Interferon | ZymoGenetics/Bristol-Myers Squibb |

Synthetic Methods

A route to prepare Compound I is shown in Scheme 1. This route utilizes Bayliss-Hillman and palladium cross coupling chemistry approaches. A Bayliss-Hillman reaction provided the unsaturated ester. DABCO or (4s)-quinuclidin-3-ol can be utilized in this initial step as the base. The hydroxy was acetylated to provide the acetate. Conjugate addition of the indole under basic conditions provided the precurser to cyclization, which is the substrate for a palladium cross coupling reaction which gave the cycloheptene. Use of dimethyl sulfoxonium ylide provided the racemic cyclopropane. This compound was resolved via SFC chiral chromatography. This separation was amenable to larger scales such as >100 g. The tert-butyl ester was treated with TFA in CH$_2$Cl$_2$ to give the acid, which was isolated as crude product after removal of CH$_2$Cl$_2$ and TFA. The crude acid was coupled with bis-HCl salt of (1R,5S)-3-methyl-3,8-diazabicyclo[3.2.1]octane in CH$_2$Cl$_2$ in the presence of HATU and Hunig's base to afford the amide after purification via column chromatography. Hydrolysis with LiOH in a mixture of MeOH and THF yielded penultimate compound after extractive work-up and trituration with CH$_2$Cl$_2$. The final coupling of the acid with 1-methylcyclopropane-1-sulfonamide facilitated by EDC and DMAP afforded Compound 1. The material obtained by column chromatography purification contained ~3% CH$_2$Cl$_2$ residual solvent which was difficult to remove under high vacuum at 80° C. CH$_2$Cl$_2$ was removed by repeatedly dissolving the API in MeOH and evaporating, and final high vacuum drying at 60° C. for 24 h.

The intermediate 1-methylcyclopropane-1-sulfonamide was prepared based on previously reported method (Synlett 2006, 5, 725-278) (Scheme 2). N-(tert-butyl)-1-methylcyclopropane-1-sulfonamide was synthesized using a one-pot procedure from N-(tert-butyl)-3-chloropropane-1-sulfonamide through n-BuLi promoted intramolecular cyclization, lithiation and alkylation with methyl iodide. The removal of the Boc protecting group with TFA afforded 1-methylcyclopropane-1-sulfonamide.

Scheme 1.

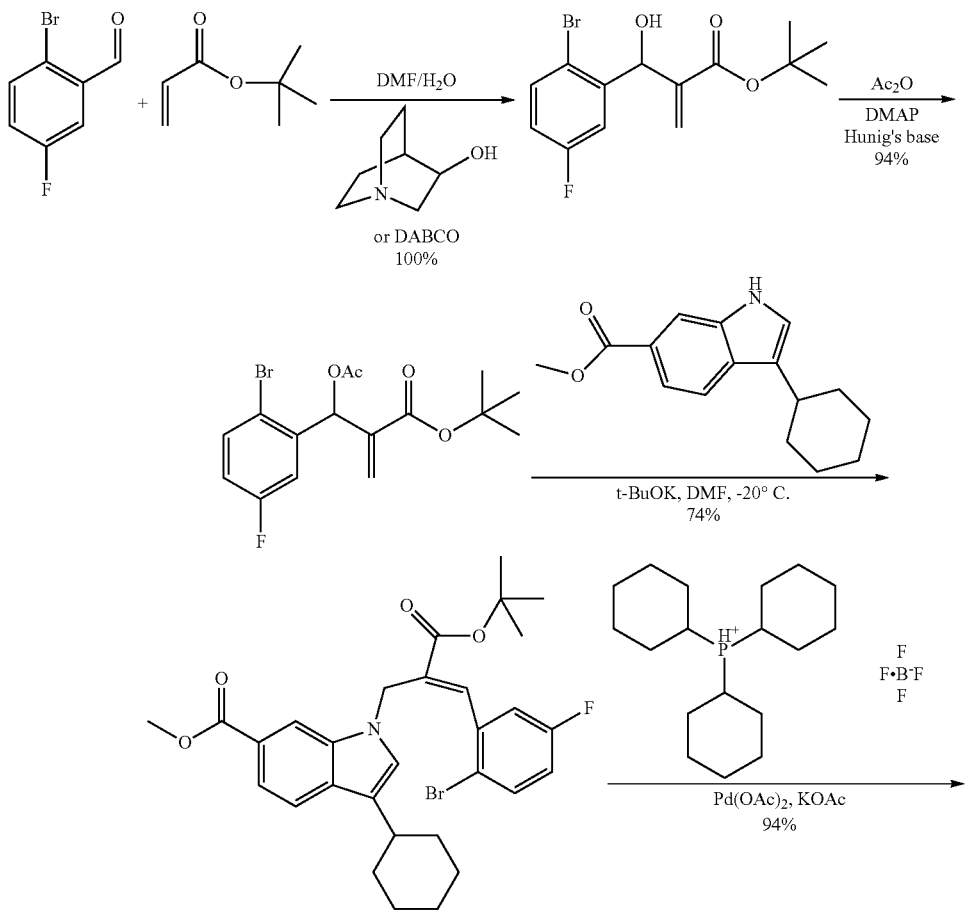

-continued
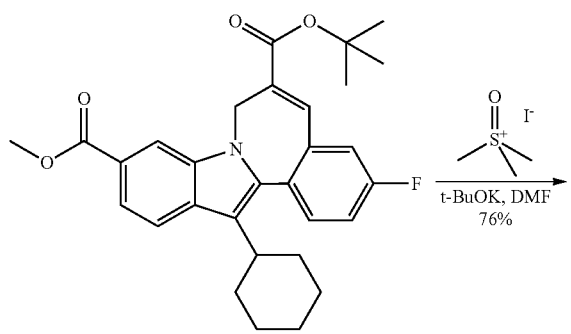
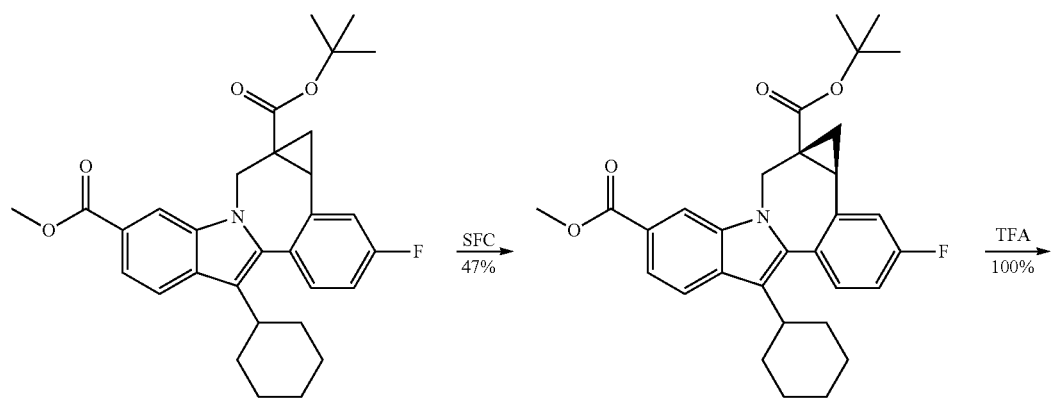
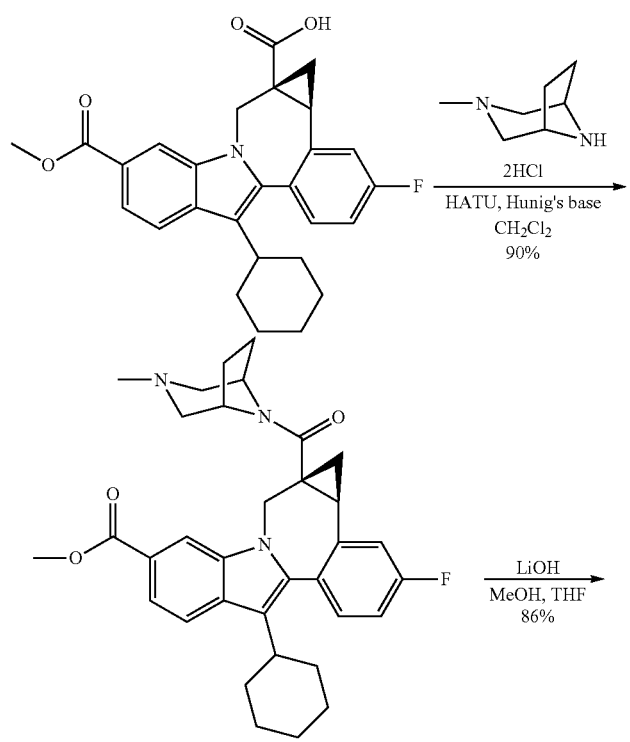

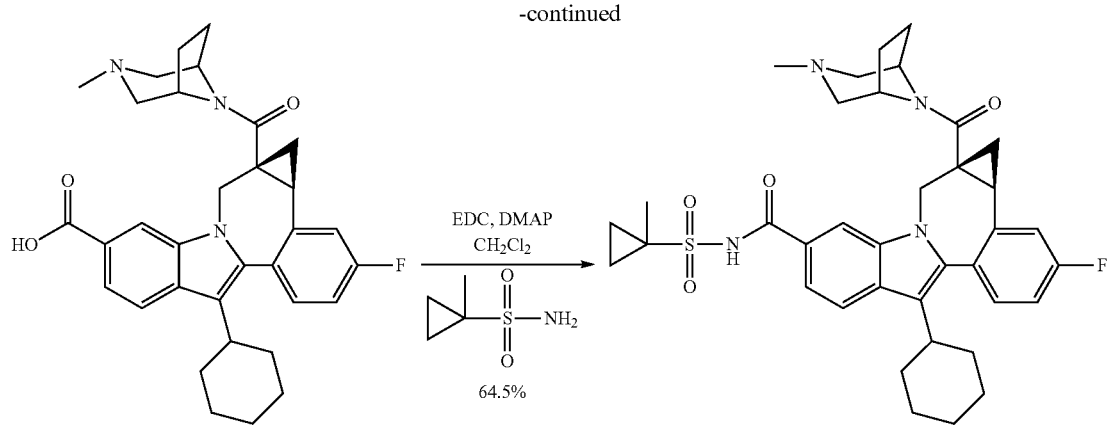

Scheme 2

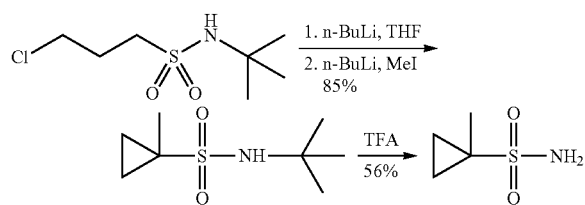

PREPARATION 1 tert-butyl 2-((2-bromo-5-fluorophenyl)(hydroxy)methyl)acrylate

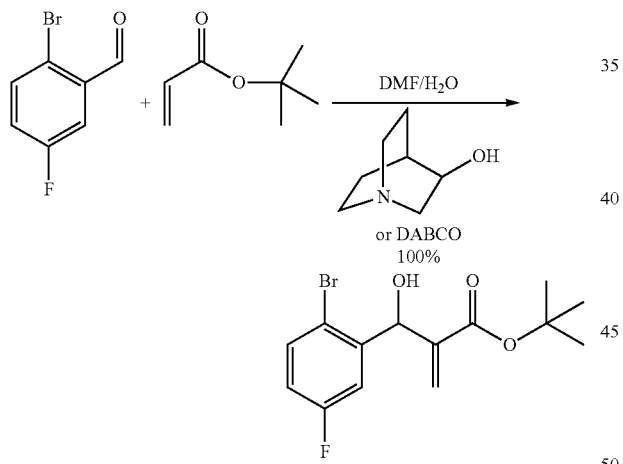

In a 1 L flask was added 2-bromo-5-fluorobenzaldehyde (10.0 g, 49.3 mmol), (4s)-quinuclidin-3-ol (6.26 g, 49.3 mmol) in DMF (28 mL) and water (12 mL). To this reaction mixture was added tert-butyl acrylate (14.3 mL, 99.0 mmol). The mixture was then stirred at rt for 19 h. At this time LCMS indicated consumption of starting materials. The reaction mixture was diluted with ether (500 mL) and the layers were separated. The aqueous layer was extracted twice with ether (200 mL each). The combined organic phases were washed with 0.1N HCl, water and brine. It was then dried over MgSO4, filtered and concentrated to yield 18.0 g (>100%) of the product as a yellow oil. 1H NMR (400 MHz, CDCl$_3$) δ 7.53 (dd, J=8.8, 5.3 Hz, 1H), 7.32 (dd, J=9.7, 3.1 Hz, 1H), 6.93 (ddd, J=8.7, 7.7, 3.1 Hz, 1H), 6.29 (s, 1H), 5.85 (s, 1H), 5.52 (t, J=1.1 Hz, 1H), 1.50 (s, 9H). LCMS: (RT=2.06 min), Column: PHENOMENEX-LUNA 2.0×30 mm (3 μm), Mobile Phase: gradient 0-100% B, Solvent A (90% Water: 10% Methanol: 0.1% TFA), Solvent B (10% Water: 90% Methanol: 0.1% TFA), Flow rate: 1.0 mL/min; (M+H+23)= 355.09.

Alternate Preparation. This procedure uses DABCO as a more economical substitute for (4s)-quinuclidin-3-ol. A 1 L flask was charged with 2-bromo-5-fluorobenzaldehyde (13.4 g, 66.0 mmol), DABCO (14.81 g, 132 mmol), DMF (53.6 mL) and water (13.4 mL). To this reaction mixture was added tert-butyl acrylate (12.68 g, 99.0 mmol). The mixture was then stirred at rt for 12 h. At this time TLC indicated consumption of starting material. The reaction mixture was diluted with 25 mL of water and then extracted with two 100 mL portions of MTBE. The combined organic phases were washed with 0.1N HCl, water and brine. It was then dried over MgSO4, filtered and concentrated to yield 25 g (>100%) of the product as a colorless oil which was used without further purification.

PREPARATION 2 tert-butyl 2-(acetoxy(2-bromo-5-fluorophenyl)methyl)acrylate

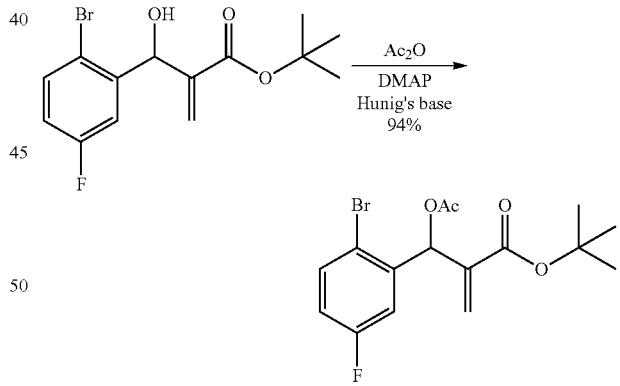

To a mixture of the hydroxy starting material (18 g, 54.4 mmol) in DCM (500 mL) was added acetic anhydride (6.15 mL, 65.2 mmol), Hunig's base (12.3 mL, 70.7 mmol) and DMAP (0.066 g, 0.54 mmol). This mixture was stirred at rt for 2 h and then concentrated in vacuo. The residue was diluted with ether (500 mL) and washed with 0.1N HCl, water and brine. The organic phase was then dried over MgSO4, filtered and concentrated in vacuo to yield 19 g (94%) of the acetate as yellow oil. 1H NMR (400 MHz, CDCl$_3$) δ 7.57 (dd, J=8.8, 5.3 Hz, 1H), 7.09 (dd, J=9.3, 3.0 Hz, 1H), 6.96 (ddd, J=8.8, 7.8, 3.0 Hz, 1H), 6.92 (d, J=0.8 Hz, 1H), 6.45-6.41 (m, 1H), 5.54-5.49 (m, 1H), 2.18-2.15 (s, 3H), 1.47-1.43 (s, 9H). LCMS: (RT=1.46 min), Column: PHENOMENEX-LUNA 2.0×30 mm (3 μm), Mobile Phase: gradient 60-100% B, Solvent A (90% Water: 10% Methanol: 0.1% TFA), Solvent B (10% Water: 90% Methanol: 0.1% TFA), Flow rate: 1.0 mL/min; (M+H+23)=397.08.

PREPARATION 3

(E)-methyl 1-(3-(2-bromo-5-fluorophenyl)-2-(tert-butoxycarbonyl)allyl)-3-cyclohexyl-1H-indole-6-carboxylate

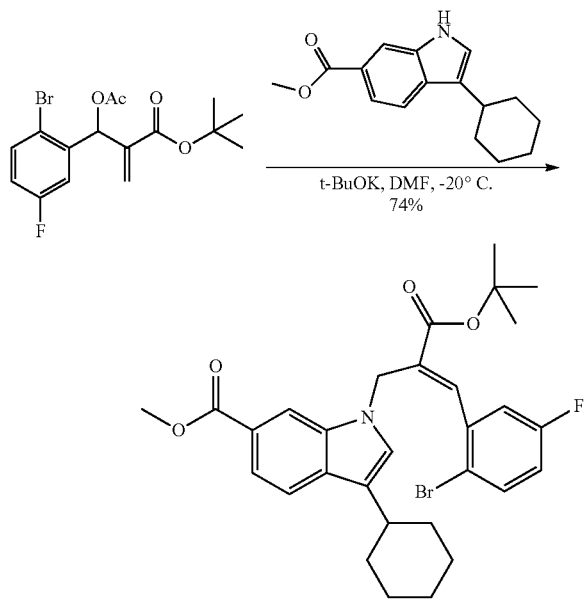

To a 500 mL flask was added the ester (4.27 g, 16.6 mmol) and DMF (100 mL). The mixture was stirred at rt until complete dissolution was achieved. Solid potassium tert-butoxide (16.6 mL, 16.6 mmol) was added over a period of 5 min. During this addition the colorless solution turned to a blue-yellow color. The reaction mixture was stirred at rt for 1 h. It was then cooled to −47° C. (acetonitrile/dry ice bath). A solution of tert-butyl 2-(acetoxy(2-bromo-5-fluorophenyl)methyl)acrylate (6.2 g, 16.61 mmol) in DMF (20 mL) was added which caused the reaction to turn to a red color. The temperature was held at −40 to −45° C. for 1 h and then warmed to −20° C. over a 2 h period. The solution turned into a light tan color. The reaction mixture was carefully quenched with ice water maintaining the temperature below −15° C. The resulting mixture was diluted with EtOAc to provide an organic and aqueous phase. The organic layer was washed with water, dried over MgSO4, filtered, and concentrated in vacuo to yield 8.0 g of the crude product as a light tan solid. It was then triturated with MeOH to isolate 7 g (74%) of the product as a white solid. 1H NMR (400 MHz, CDCl3) δ 7.78-7.83 (m, 2H), 7.75 (dd, J=1.25, 8.28 Hz, 1H), 7.58-7.64 (m, 2H), 6.89-7.00 (m, 3H), 5.02 (s, 2H), 3.94 (s, 3H), 2.73-2.85 (m, 1H), 2.04 (d, J=11.04 Hz, 2H), 1.75-1.90 (m, 3H), 1.38-1.50 (m, 5H), 1.37 (s, 9H). LCMS: (RT=0.56 min), Column: PHENOMENEX-LUNA 2.0×30 mm (3 μm), Mobile Phase: gradient 100% B, Solvent B (10% Water: 90% Methanol: 0.1% TFA), Flow rate: 1.0 mL/min; (M+H)= 572.27.

PREPARATION 4

10-methyl 6-(2-methyl-2-propanyl) 13-cyclohexyl-3-fluoro-7H-indolo[2,1-a][2]benzazepine-6,10-dicarboxylate

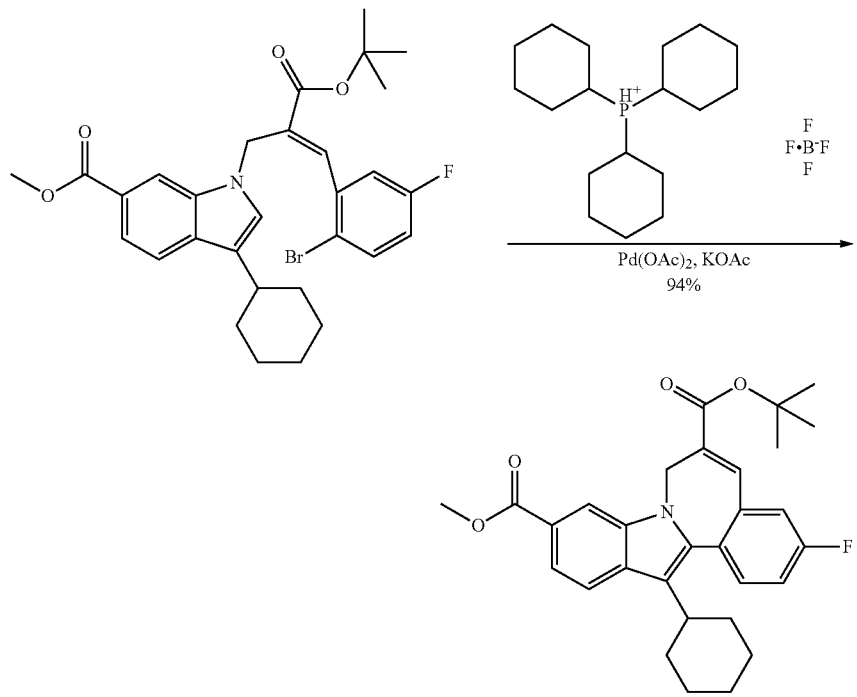

A mixture of starting material (13.0 g, 22.8 mmol), Pd(OAc)$_2$ (0.256 g, 1.14 mmol), potassium acetate (7.83 g, 80.0 mmol), tricyclohexylphosphonium tetrafluoroborate (0.629 g, 1.71 mmol) in N,N-dimethylacetamide (50 mL) was placed under a N2 atmosphere (vacuum/N2 refill for 3 times). It was then heated at 122° C. for 6 h. The reaction mixture became dark yellow/brown and some black solid precipitate was present. It was cooled to rt and diluted with EtOAc (800 mL). The mixture was then washed with water (3×), dried over MgSO4, filtered, and concentrated in vacuo to yield 12 g of a yellow solid. The solid was triturated with hexane to give 10.5 g (94%) of the product as a yellow solid. 1H NMR (400 MHz, CDCl3) δ 8.31 (d, J=1.0 Hz, 1H), 7.90 (d, J=8.5 Hz, 1H), 7.78 (dd, J=8.5, 1.5 Hz, 1H), 7.74 (s, 1H), 7.60 (dd, J=8.5, 5.8 Hz, 1H), 7.24 (td, J=9.0, 2.8 Hz, 2H), 5.77-5.55 (m, 1H), 4.15 (m, 1H), 3.98 (s, 3H), 2.88-2.77 (m, 1H), 2.19-1.33 (m, 10H), 1.66 (s, 9H). LCMS: (RT=0.66 min), Column: PHENOMENEX-LUNA 2.0×30 mm (3 μm), Mobile Phase: gradient 100% B, Solvent B (10% Water: 90% Methanol: 0.1% TFA), Flow rate: 1.0 mL/min; (M+H)=490.35.

PREPARATION 5

5-methyl 1a-(2-methyl-2-propanyl)(1aR,12bS)-8-cyclohexyl-11-fluoro-1,12b-dihydrocyclopropa[d]indolo[2,1-a][2]benzazepine-1a,5(2H)-dicarboxylate

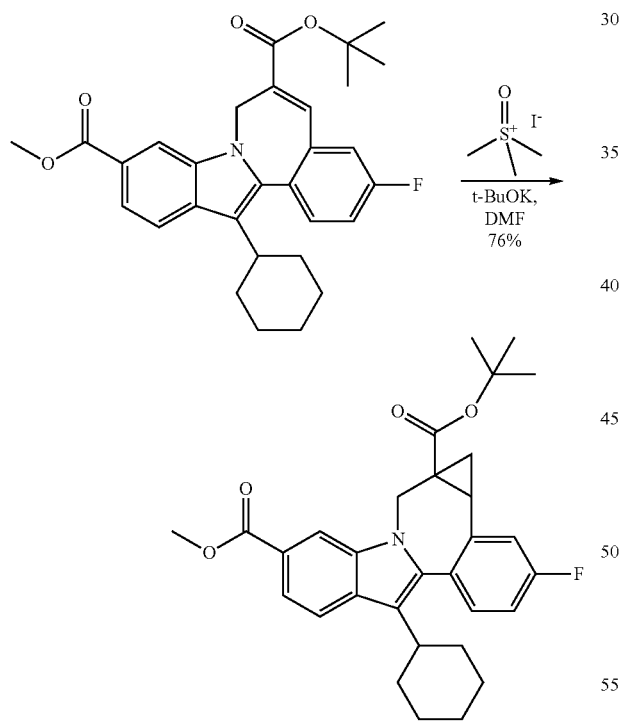

To a mixture trimethylsulfoxonium iodide (1.68 g, 7.64 mmol) in DMF (10 mL) was added potassium tert-butoxide (7.64 mL, 7.64 mmol). The mixture was stirred at rt for 1 h. The starting material (3.4 g, 6.94 mmol) was added to the reaction mixture and stirring was continued for another 2 h. A tan precipitate was formed. Water (20 mL) was added to the reaction mixture and the resulting off-white solid was collected by filtration and washed with water. This crude product was dried in vacuo to obtain 2.9 g of an off-white solid which was triturated with hexane to give 2.7 g of the racemic diester the product as a white solid. 1H NMR (400 MHz, CDCl$_3$) (rotamers) δ 8.32 (d, J=1.0 Hz, 0.5H), 8.17 (s, 0.5H), 7.91-7.84 (m, 1H), 7.81-7.73 (m, 1H), 7.38-7.29 (m, 1.5H), 7.24 (dd, J=9.7, 2.6 Hz, 0.5H), 7.09 (tt, J=8.3, 2.5 Hz, 1H), 5.45 (d, J=15.6 Hz, 0.5H), 5.18 (d, J=15.3 Hz, 0.5H), 4.06 (d, J=15.1 Hz, 0.5H), 3.99 (s, 1.5H), 3.97 (s, 1.5H), 3.43 (d, J=15.1 Hz, 0.5H), 2.96-2.86 (m, 1H), 2.83-2.73 (m, 0.5H), 2.59 (dd, J=10.0, 6.8 Hz, 0.5H), 2.18-1.27 (m, 11H), 1.55 (s, 4.5H), 1.31 (s, 4.5H), 1.16 (dd, J=6.0, 4.3 Hz, 0.5H), 0.37 (t, J=6.1 Hz, 0.5H). LCMS: (RT=0.57 min), Column: PHENOMENEX-LUNA 2.0×30 mm (3 μm), Mobile Phase: gradient 100% B, Solvent B (10% Water: 90% Methanol: 0.1% TFA), Flow rate: 1.0 mL/min; (M+H)=504.39.

PREPARATION 6

5-methyl 1a-(2-methyl-2-propanyl)(1aR,12bS)-8-cyclohexyl-11-fluoro-1,12b-dihydrocyclopropa[d]indolo[2,1-a][2]benzazepine-1a,5(2H)-dicarboxylate

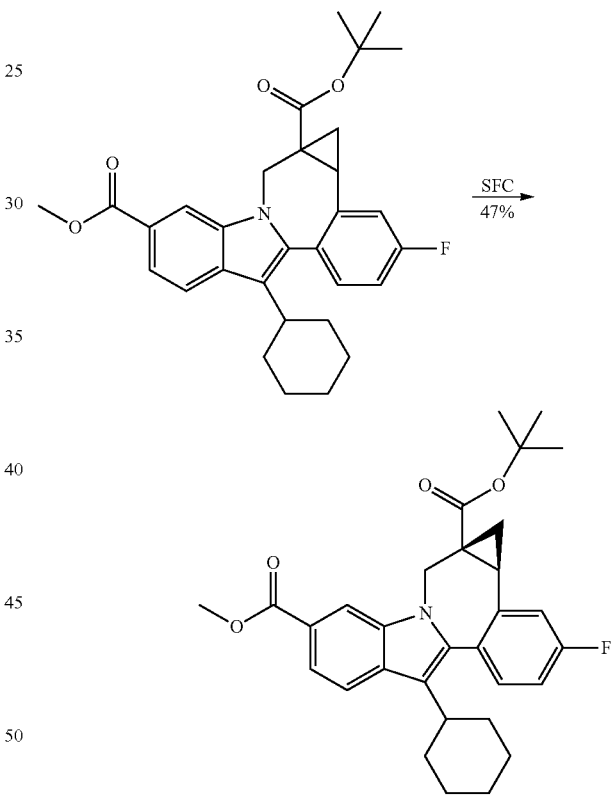

Racemic compound was chirally separated to yield 1.35 g as a white solid. The following conditions were used for the chiral separation and the faster eluting compound was the desired enantiomer. Column: ChiralPak AD-H, 30×250 mm, 5 mm; Mobile Phase: 20% MeOH/80% CO2; Pressure: 150 bar; Temperature: 35° C.; Flow Rate: 70 mL/min; UV: 210 nm. 1H NMR (500 MHz, CDCl$_3$) (rotamers) δ 8.34-8.29 (m, 0.5H), 8.17 (s, 0.5H), 7.91-7.85 (m, 1H), 7.78 (dd, J=18.8, 1.4 Hz, 1H), 7.38-7.21 (m, 2H), 7.14-7.05 (m, 1H), 5.50-5.41 (m, 0.5H), 5.22-5.15 (m, 0.5H), 4.06 (d, J=15.3 Hz, 0.5H), 3.99 (s, 1.5H), 3.97 (s, 1.5H), 3.48-3.39 (m, 0.5H), 2.96-2.86 (m, 1H), 2.81-2.72 (m, 0.5H), 2.63-2.53 (m, 0.5H), 2.18-1.24 (m, 11H), 1.55 (s, 4.5H), 1.32 (s, 4.5H), 1.16 (dd, J=6.1, 4.3 Hz, 0.5H), 0.38 (t, J=6.1 Hz, 0.5H).

PREPARATION 7

(1aS,12bR)-8-cyclohexyl-11-fluoro-5-(methoxycarbonyl)-1,12b-dihydrocyclopropa[d]indolo[2,1-a][2]benzazepine-1a(2H)-carboxylic acid

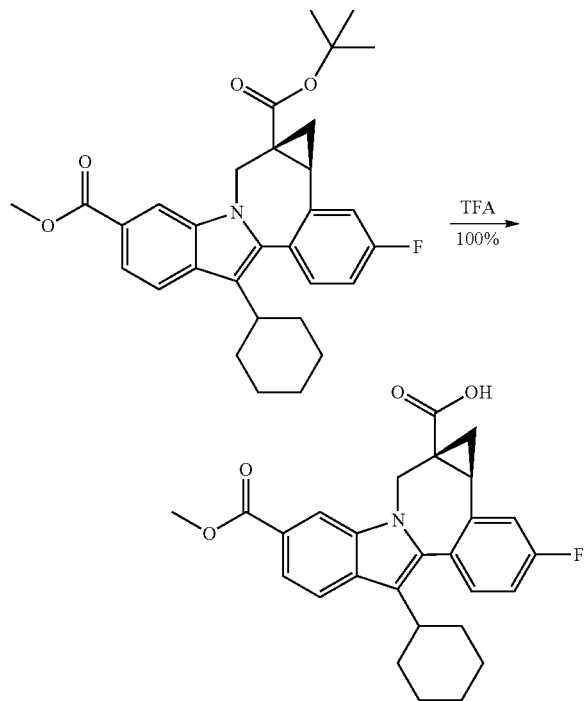

A mixture of starting material (700 mg, 1.39 mmol) and TFA (5 mL, 64.9 mmol) was stirred at rt for 3 h. LCMS indicated complete consumption of the diester. The reaction mixture was then concentrated in vacuo to yield 630 mg (100%) of the product as an off-white solid. 1H NMR (400 MHz, CDCl₃)(rotamers) δ 8.41 (d, J=1.0 Hz, 0.6H), 8.16 (s, 0.4H), 7.91 (d, J=8.8 Hz, 0.4H), 7.85 (d, J=8.5 Hz, 0.6H), 7.75 (dd, J=8.4, 1.4 Hz, 0.4H), 7.67 (dd, J=8.4, 1.4 Hz, 0.6H), 7.49-7.34 (m, 2H), 7.25-7.13 (m, 1H), 5.50 (d, J=15.6 Hz, 0.6H), 5.28 (d, J=15.1 Hz, 0.4H), 4.05 (d, J=15.1 Hz, 0.4H), 3.96 (s, 1.2H), 3.95 (s, 1.8H), 3.52-3.45 (m, 0.6H), 3.00-2.74 (m, 2H), 2.23-1.23 (m, 11.6H), 0.24 (t, J=6.0 Hz, 0.4H); LCMS: (RT=2.60 min), Column: PHENOMENEX-LUNA 2.0×30 mm (3 μm), Mobile Phase: gradient 0-100% B, Solvent A (90% Water: 10% Methanol: 0.1% TFA), Solvent B (10% Water: 90% Methanol: 0.1% TFA), Flow rate: 1.0 mL/min (M+H)=448.29.

PREPARATION 8 methyl(1aR,12bS)-8-cyclohexyl-11-fluoro-1a-((3-methyl-3,8-diazabicyclo[3.2.1]oct-8-yl)carbonyl)-1,1a,2,12b-tetrahydrocyclopropa[d]indolo[2,1-a][2]benzazepine-5-carboxylate

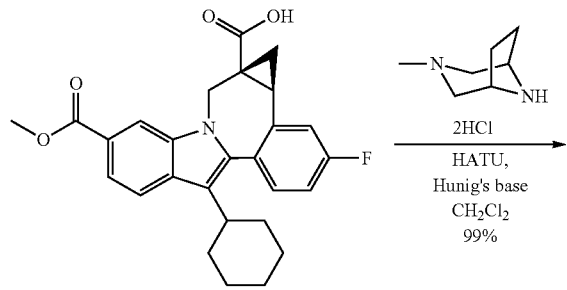

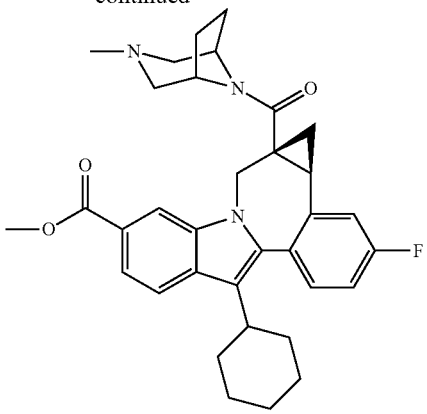

A mixture of starting acid (300 mg, 0.670 mmol), (1R,5S)-3-methyl-3,8-diazabicyclo[3.2.1]octane bishydrochloride (160 mg, 0.804 mmol), 2-(1H-benzo[d][1,2,3]triazol-1-yl)-1,1,3,3-tetramethylisouronium tetrafluoroborate (HATU) (258 mg, 0.804 mmol) and N-ethyl-N-isopropylpropan-2-amine (Hunig's base)(0.467 mL, 2.68 mmol) in DCM (4 mL) was stirred at rt for 2 h. The reaction mixture was then concentrated in vacuo. The residue was diluted with EtOAc, washed with water (5×), dried (MgSO4), filtered, and concentrated in vacuo to yield 370 mg (99%) of the product as a light yellow solid. 1H NMR (500 MHz, DMSO-d6) (rotamers) δ 8.17 (s, 0.35H), 8.03 (s, 0.65H), 7.93 (d, J=8.5 Hz, 0.35H), 7.89 (d, J=8.4 Hz, 0.65H), 7.69 (dd, J=8.5, 1.3 Hz, 0.35H), 7.62 (dd, J=8.5, 1.3 Hz, 0.65H), 7.51-7.25 (m, 3H), 5.12 (d, J=15.6 Hz, 0.65H), 4.94 (d, J=15.1 Hz, 0.35H), 4.32 (br s, 1H), 4.11 (d, J=15.3 Hz, 0.35H), 4.03-3.96 (m, 0.65H), 3.90 (s, 1H), 3.88 (s, 2H), 3.64 (br s, 0.35H), 3.61 (d, J=15.4 Hz, 0.65H), 2.94-2.84 (m, 1H), 2.79-1.05 (m, 24H). LCMS: (RT=2.26 min), Column: PHENOMENEX-LUNA 2.0×30 mm (3 μm), Mobile Phase: gradient 0-100% B, Solvent A (90% Water: 10% Methanol: 0.1% TFA), Solvent B (10% Water: 90% Methanol: 0.1% TFA), Flow rate: 1.0 mL/min; (M+H)=556.50.

PREPARATION 9

(1aR,12bS)-8-cyclohexyl-11-fluoro-1a-((3-methyl-3,8-diazabicyclo[3.2.1]oct-8-yl)carbonyl)-1,1a,2,12b-tetrahydrocyclopropa[d]indolo[2,1-a][2]benzazepine-5-carboxylic acid

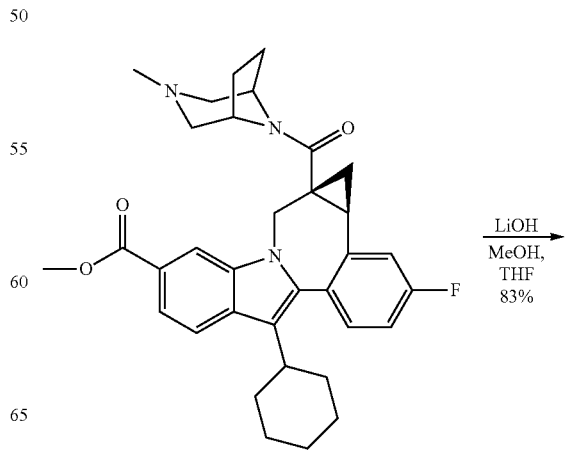

27

-continued

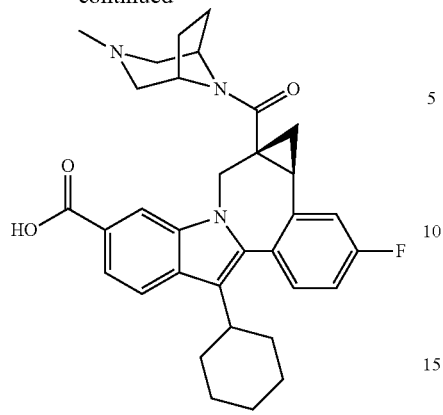

A mixture of the ester (400 mg, 0.720 mmol), 1N NaOH (3.60 mL, 3.60 mmol) and MeOH (4 mL) was refluxed for 3 h. It was then concentrated in vacuo. The residue was diluted with water and acidified with 1N HCl until reaching pH=4. The white precipitate which formed was collected by filtration and washed with water. The white solid was dried to yield 360 mg (83%) of the product as an off-white solid. 1H NMR (500 MHz, DMSO-d6)(rotamers) δ 8.16 (s, 0.35H), 8.02 (s, 0.65H), 7.90 (d, J=8.4 Hz, 0.35H), 7.86 (d, J=8.4 Hz, 0.65H), 7.69 (d, J=8.4 Hz, 0.35H), 7.63 (d, J=8.4 Hz, 0.65H), 7.51-7.38 (m, 2H), 7.34-7.24 (m, 1H), 5.15 (d, J=15.3 Hz, 0.65H), 4.99 (d, J=16.2 Hz, 0.35H), 4.56-4.40 (m, 1H), 4.18-4.06 (m, 1H), 3.65-3.57 (m, 1H), 2.94-2.84 (m, 1H), 2.79-1.15 (m, 24H). LCMS: (RT=2.19 min), Column: PHENOMENEX-LUNA 2.0×30 mm (3 μm), Mobile Phase: gradient 0-100% B, Solvent A (90% Water: 10% Methanol: 0.1% TFA), Solvent B (10% Water: 90% Methanol: 0.1% TFA), Flow rate: 1.0 mL/min; (M+H)=542.52.

PREPARATION 10

(1aR,12bS)-8-cyclohexyl-11-fluoro-N-((1-methylcyclopropyl)sulfonyl)-1a-((3-methyl-3,8-diazabicyclo[3.2.1]oct-8-yl)carbonyl)-1,1a,2,12b-tetrahydrocyclopropa[d]indolo[2,1-a][2]benzazepine-5-carboxamide

28

-continued

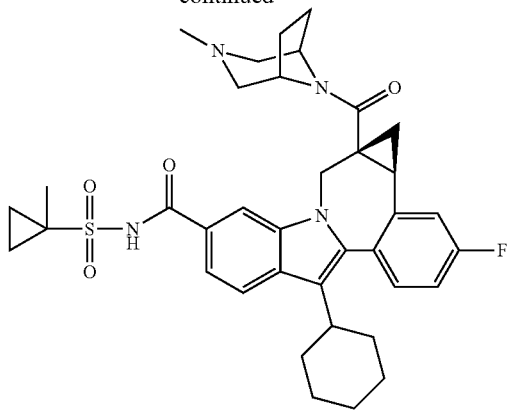

A mixture of the starting acid (40 mg, 0.074 mmol), 1-methylcyclopropane-1-sulfonamide (20.0 mg, 0.15 mmol), EDC (28 mg, 0.15 mmol), DMAP (27 mg, 0.22 mmol) in DCM (2 mL) was stirred at rt for 16 h. It was then concentrated and purified by preparative HPLC (Column: Waters Sunfire C18 OBD 30×100 mm, Gradient: 50-75% B, Solvent A: 90% Water: 10% Methanol: 0.1% TFA, Solvent B: 10% Water: 90% Methanol: 0.1% TFA, Gradient Time=18 min, Stop Time=20 min, Flow Rate=25 ml/min, UV detection, Wavelength: 220 nm) to give 31 mg (61%) of the product as a white solid. 1H NMR (500 MHz, CDCl₃)(major rotamer) δ 8.01 (br s, 1H), 7.88 (d, J=7.9 Hz, 1H), 7.58 (br d, 1H), 7.36 (m, 1H) 7.29 (d, J=2.5 Hz 1H), 7.20 (dd, J=9.5, 2.5 Hz, 1H), 7.10-7.06 (m, 1H), 5.20 (d, J=15.1 Hz, 1H), 4.42 (br s, 1H), 4.15 (d, J=14.5 Hz, 1H), 3.58 (d, J=15.4 Hz, 1H), 3.39 (br s, 1H), 2.91 (t, J=12.0 Hz, 1H), 2.74 (m, 1H), 2.70 (m, 1H), 2.56 (br s, 1H), 2.22 (m, 1H), 1.99 (m, 2H), 1.98 (m, 2H), 1.82 (m, 2H), 1.55 (m, 2H), 1.50 (m, 5H), 1.25 (m 2H), 1.20 (t, J=6.1 Hz, 1H), 0.95 (m, 4H). LCMS: (RT=2.16 min), Column: PHENOMENEX-LUNA 2.0×30 mm (3 μm), Mobile Phase: gradient 0-100% B, Solvent A (90% Water: 10% Methanol: 0.1% TFA), Solvent B (10% Water: 90% Methanol: 0.1% TFA), Flow rate: 1.0 mL/min; (M+H)=659.27.

PREPARATION 11

5-methyl 1a-(2-methyl-2-propanyl)(1aR,12bS)-8-cyclohexyl-11-fluoro-1,12b-dihydrocyclopropa[d]indolo[2,1-a][2]benzazepine-1a,5(2H)-dicarboxylate

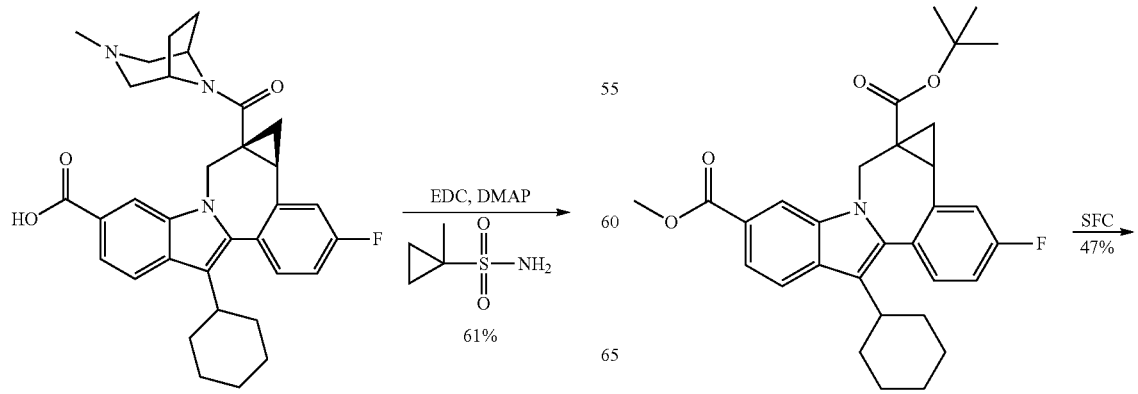

-continued

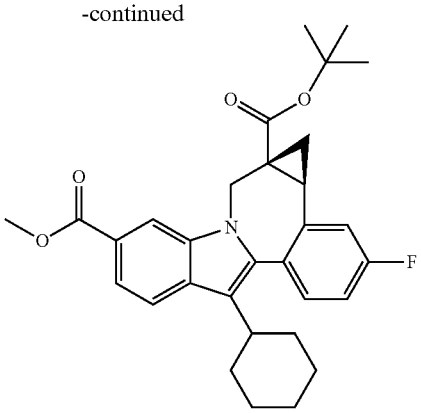

Conditions used for the SFC separation of enantiomers on preparative scale are described below. A single 580 g batch of racemic product was divided and separated in two runs as described below. 275.6 grams was separated using the following preparative SFC conditions. The purity of the target isomer fraction was determined by the analytical SFC conditions. The yield of the target isomer is approximately 120 grams. 211.8 grams was separated using the following preparative SFC conditions. The purity of the target isomer fraction was determined by the analytical SFC conditions. The yield of the target isomer is approximately 102 grams. Chiral purity of the target isomer from both runs was ≧99.9%.

PREPARATION 12

(1aS,12bR)-8-cyclohexyl-11-fluoro-5-(methoxycarbonyl)-1,12b-dihydrocyclopropa[d]indolo[2,1-a][2]benzazepine-1a(2H)-carboxylic acid

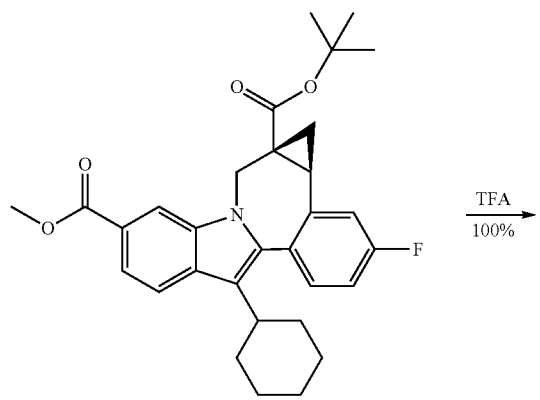

To a solution of starting material (87 g, 173 mmol) in CH$_2$Cl$_2$ (870 mL) cooled with an ice bath was added trifluoroacetic acid (394 g, 3455 mmol). The reaction mixture was allowed to warm to rt and stirred for 22 h. The solvent and TFA were removed and the residue was dissolved in CH$_2$Cl$_2$ (1000 mL). The solution was washed with water (4×500 mL), brine (500 mL), dried over MgSO$_4$, filtered and concentrated in vacuo and high vacuum to give the crude product (4bS,5aR)-12-cyclohexyl-3-fluoro-9-(methoxycarbonyl)-4b,5,5a,6-tetrahydrobenzo[3,4]cyclopropa-[5,6]azepino[1,2-a]indole-5a-carboxylic acid (79 g, 177 mmol, 102% yield) as a yellow oil which was used for the next step without further purification. $^1$H NMR (400 MHz, CDCl$_3$) δ 8.39 (s, 0.5 H), 8.17 (bs, 1.5 H), 7.86-7.90 (m, 1 H), 7.73-7.81 (m, 1 H), 7.23-7.38 (m, 2 H), 7.10-7.16 (m, 1 H), 5.48 (d, J=16.0 Hz, 0.5 H), 5.24 (d, J=16.0 Hz, 0.5 H), 4.08-4.20 (m, 1 H), 4.0 (s, 3 H), 3.98 (d, J=16.0 Hz, 0.5 H), 3.46 (d, J=16.0 Hz, 0.5 H), 2.90-3.03 (m, 1 H), 2.75-2.80 (m, 1 H), 1.21-2.18 (m, 10 H), 0.89-0.93 (m, 0.5 H), 0.50-0.53 (m, 0.5 H).

PREPARATION 13 methyl(1aR,12bS)-8-cyclohexyl-11-fluoro-1a-((3-methyl-3,8-diazabicyclo[3.2.1]oct-8-yl)carbonyl)-1,1a,2,12b-tetrahydrocyclopropa[d]indolo[2,1-a][2]benzazepine-5-carboxylate

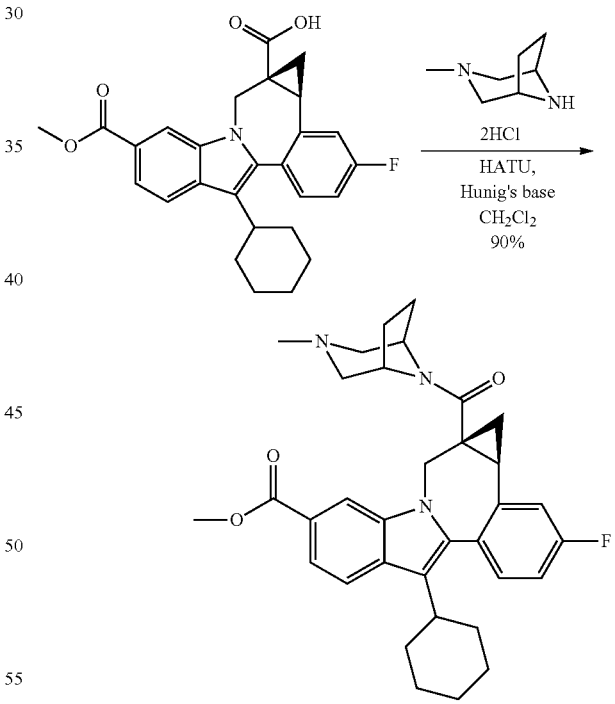

To a N$_2$ flushed, three necked, 3 L round bottom flask was added starting acid (79 g, 177 mmol), CH$_2$Cl$_2$ (1000 mL), bis-HCl salt of (1R,5S)-3-methyl-3,8-diazabicyclo[3.2.1]octane (42.23 g, 212 mmol), O-(7-azabenzotriazol-1-yl)-N,N,N',N'-tetramethyluronium hexafluorophosphate (81 g, 212 mmol) and N,N-di-iso-propylethylamine (123 mL, 706 mmol) respectively. The reaction mixture was stirred at rt for 3 h. It was diluted with water (1000 mL). After stirring for 10 mins, the organic phase was separated and the aqueous layer was extracted with CH$_2$Cl$_2$ (500 mL). The combined organic extracts were washed with water (2×1000 mL), brine (1000 mL), dried over MgSO$_4$, filtered and concentrated in vacuo to ~200 mL. The solution was then subjected to a flash silica gel column (packed with hexane) using 3% TEA/30 to 70% EtOAc in hexane to give the product (88 g, 158 mmol, 90% yield) as a yellow foam. $^1$H NMR (500 MHz, CDCl$_3$) δ 8.12 (bs, 0.5 H), 8.08 (bs, 0.5 H), 7.87-7.92 (m, 1 H), 7.76-7.83 (m, 1 H), 7.28-7.36 (m, 2 H), 7.08-7.15 (m, 1 H), 5.21 (d, J=15.0 Hz, 0.5 H), 4.24 (d, J=15.0 Hz, 0.5H), 4.12-4.17 (m, 1.5H), 3.93-3.98 (m, 3.5H), 3.61 (d, J=15.0 Hz, 0.5 H), 3.38 (bs, 0.5 H), 2.94 (t, J=15.0 Hz, 1H), 2.72-2.81 (m, 2 H), 1.06-2.52 (m, 22 H).

PREPARATION 14

(1aR,12bS)-8-cyclohexyl-11-fluoro-1a-((3-methyl-3,8-diazabicyclo[3.2.1]oct-8-yl)carbonyl)-1,1a,2,12b-tetrahydrocyclopropa[d]indolo[2,1-a][2]benzazepine-5-carboxylic acid

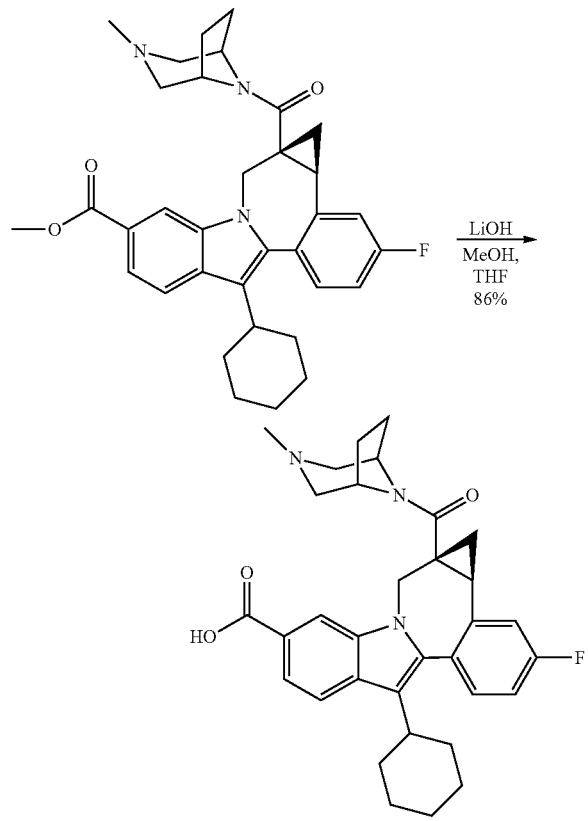

To a solution of starting ester (50 g, 90 mmol) in THF (400 mL) and MeOH (100 mL) was added a solution of lithium hydroxide (10.77 g, 450 mmol) in water (100 mL). The mixture was heated to 50° C. for 16 h. HPLC indicated the completion of the reaction. After cooling, the organic solvents were removed and the residual yellow slurry was extracted with EtOAc (2×400 mL). The combined organic extracts were washed with brine (500 mL), dried over Na$_2$SO$_4$, filtered and concentrated in vacuo to give a crude solid which was triturated with CH$_2$Cl$_2$ (80 mL, rt to −20° C.) to afford the product (41.76 g, 77 mmol, 86% yield) as a white solid. 99.8% HPLC area purity. $^1$H NMR (300 MHz, DMSO-d$_6$) δ 8.00 (bs, 1 H), 7.79 (t, J=9.0 Hz, 1 H), 7.58-7.66 (m, 1 H), 7.26-7.32 (m, 2 H), 7.07-7.17 (m, 1H), 4.79-5.07 (m, 1 H), 4.04-4.26 (m, 2 H), 3.88 (bs, 1 H), 3.57 (d, J=15 Hz, 1 H), 3.21 (s, 3 H), 1.03 -2.89 (m, 21 H).

PREPARATION 15

(1aR,12bS)-8-cyclohexyl-11-fluoro-N-((1-methylcyclopropyl)sulfonyl)-1a-((3-methyl-3,8-diazabicyclo[3.2.1]oct-8-yl)carbonyl)-1,1a,2,12b-tetrahydrocyclopropa[d]indolo[2,1-a][2]benzazepine-5-carboxamide

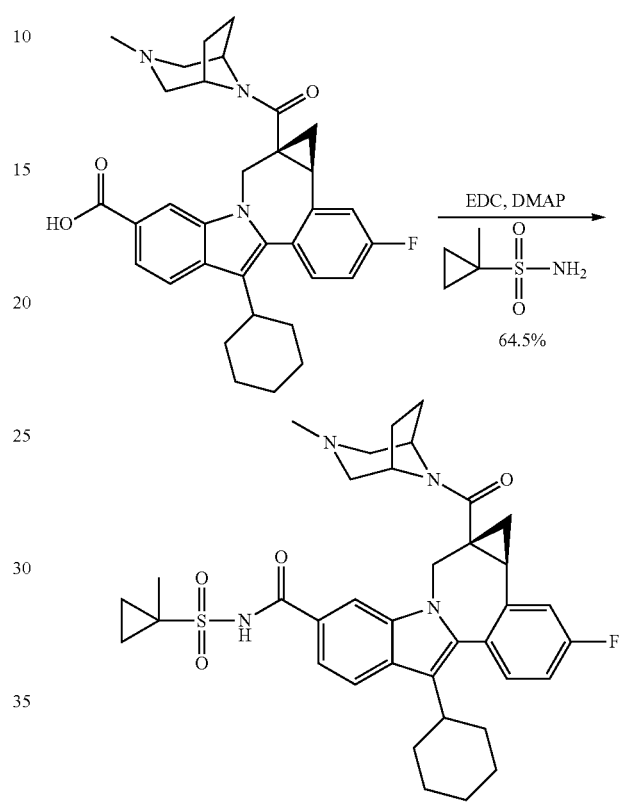

A mixture of starting material (27.3 g, 50.4 mmol), 1-methylcyclopropane-1-sulfonamide (20.44 g, 151 mmol), 4-dimethylaminopyridine (24.63 g, 202 mmol) and EDC (29.0 g, 151 mmol) in CH$_2$Cl$_2$ (250 mL) was stirred at rt for 72 h. The mixture was acidified with 1 N HCl (~200 mL) to PH=4. After stirring for 30 mins, the organic phase was separated and the aqueous layer was extracted with CH$_2$Cl$_2$ (200 mL). The combined organic extracts were washed with water (3×250 mL, small amount of NaCl was added to help separation), brine (250 mL), dried over MgSO$_4$, filtered and concentrated in vacuo to give a crude mixture which was dissolved in CH$_2$Cl$_2$ (100 mL). The solution was subjected to a silica gel column using 3% MeOH in CH$_2$CH$_2$ as the eluent to yield the product as a white solid (21.5 g, 32.5 mmol, 64.5% yield). 99.8% HPLC area purity. The above solid contained ~3% CH$_2$Cl$_2$. It was dissolved in MeOH (50 mL) and the solvent was evaporated in vacuo. The dried material was redissolved in MeOH (50 mL) and the solvent was removed in vacuo to give a residue which was dried in a high vacuo oven at 60° C. for 24 h to yield the product (21 g) as an off white solid. $^1$H NMR (500 MHz, CDCl$_3$) δ 8.01 (bs, 1 H), 7.88 (d, J=7.9 Hz, 1 H), 7.58 (bs, 1 H), 7.36 (m, 1H), 7.29 (d, J=2.5 Hz, 1 H), 7.20 (dd, J=9.5 and 2.5 Hz, 1 H), 7.06-7.10 (m, 1H), 5.20 (d, J=15.1 Hz, 1 H), 4.42 (bs, 1 H), 4.15 (d, J=14.5 Hz, 1 H), 3.58 (d, J=15.4 Hz, 1 H), 3.39 (bs, 1 H), 2.91 (t, J=12.0 Hz, 1 H), 2.74 (m, 1 H), 2.70 (m, 1 H), 2.56 (bs, 1 H), 2.22 (m, 1 H), 1.99 (m, 2 H), 1.98 (m, 2 H), 1.82 (m, 2H), 1.55 (m, 2 H), 1.50 (m, 5 H), 1.25 (m, 2 H), 1.20 (t, J=6.1 Hz, 1 H), 0.95 (m, 4 H).

PREPARATION 16

N-(tert-butyl)-1-methylcyclopropane-1-sulfonamide

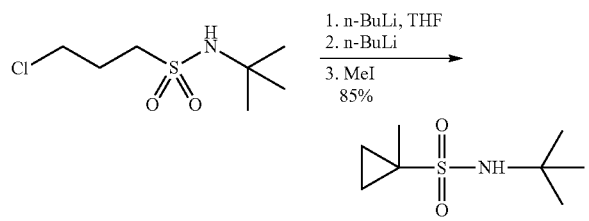

To a four necked, 5 L round bottom flask was added N-(tert-butyl)-3-chloropropane-1-sulfonamide (Previously dried by azeotroping with 3×100 mL toluene) (100 g, 468 mmol) and THF (1500 mL). This was cooled to an internal temperature of −69° C. then butyl lithium (2.5M in hexanes, 412 mL, 1.02 mol) was added dropwise over a period of 55 min while keeping the internal temperature below −65° C. The ice bath was removed and the reaction mixture was warmed to rt over 1.5 h and then cooled back down to an internal temperature of −69° C. Butyl lithium (196 mL, 515 mmol) was added to the reaction mixture over a period of 25 min while keeping the internal temperature below −65° C. The reaction mixture was then warmed to rt over the course of 1.5 h. The reaction mixture was recooled to an internal temperature of −69° C. and iodomethane (58.5 mL, 936 mmol) was added dropwise over a period of 40 min while keeping the internal temperature below −65° C. The reaction mixture was then warmed to an internal temperature of −50° C. over the course of 4 h. The cold bath was removed and a solution of saturated NH$_4$Cl (1000 mL) was added. The quenched reaction mixture was transferred to a separatory funnel along with ethyl acetate (100 mL) and water (500 mL). The layers were separated and the aqueous layer was extracted with ethyl acetate. (3×75 mL). The combined organic layers were washed with brine (700 mL), dried with MgSO$_4$, and concentrated in vacuo to an off white solid which was dried under high vac for 30 min to yield N-(tert-butyl)-1-methylcyclopropane-1-sulfonamide as a white solid (88.5 g, 99% yield). $^1$H NMR (500 MHz, CDCl$_3$) δ 4.07 (bs, 1 H), 1.51 (s, 3 H), 1.38-1.41 (m, 2 H), 1.36 (s, 9 H), 0.77-0.80 (m, 2 H).

PREPARATION 17

1-methylcyclopropane-1-sulfonamide

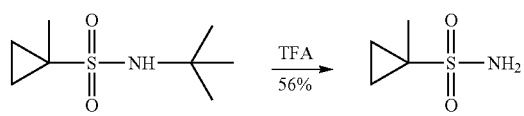

To a one necked, 1 L round bottom flask was added N-(tert-butyl)-1-methylcyclopropane-1-sulfonamide (78.6 g, 411 mmol) and TFA (340 mL). The brown solution was stirred overnight at rt. The reaction mixture was concentrated (at 50° C.) to a brown oil. A stream of N$_2$ was blown into the oil for about 35 minutes at the end of which a brown semi-solid formed. The semi-solid was suspended in ethyl acetate (80 mL) and hexane (231 mL). The suspension was stirred at rt for 10 minutes then vacuum filtered. The filter cake was rinsed with hexane then dried overnight to give a crude tan solid (51.6 g). The solid was recrystallized from a mixture of ethyl acetate (190 mL) and hexane (270 mL), (heat to reflux, cooled to rt and vacuum filtered at rt) to give an off white solid (37.6 g, 68% yield). The off white solid (37.6 g) was dissolved in hot ethyl acetate (257 mL), diluted with hexane (177 mL) then refluxed for 5 minutes. The hot solution was cooled to rt, the resulting white suspension was vacuum filtered, and the filter cake was dried to a white solid (56.6 g, 416 mmol, 56% yield). $^1$H NMR (500 MHz, DMSO-d$_6$) δ 6.72 (bs, 2 H), 1.44 (s, 3 H), 1.13 (dd, J=6.1 and 4.0 Hz, 2 H), 0.74 (dd, J=6.1 and 4.0 Hz, 2 H). $^{13}$C NMR (125 MHz, DMSO-d$_6$) δ 36.4, 17.6, 12.1.

Compound I was evaluated for antiviral activity as determined by the following assays:

Biological Methods

HCV NS5B RdRp Cloning, Expression, and Purification

The cDNA encoding the NS5B protein of HCV, genotype 1b, was cloned into the pET21a expression vector. The protein was expressed with an 18 amino acid C-terminal truncation to enhance the solubility. The E. coli competent cell line BL21(DE3) was used for expression of the protein. Cultures were grown at 37° C. for ~4 hours until the cultures reached an optical density of 2.0 at 600 nm. The cultures were cooled to 20° C. and induced with 1 mM IPTG. Fresh ampicillin was added to a final concentration of 50 μg/mL and the cells were grown overnight at 20° C.

Cell pellets (3 L) were lysed for purification to yield 15-24 mgs of purified NS5B. The lysis buffer consisted of 20 mM Tris-HCl, pH 7.4, 500 mM NaCl, 0.5% triton X-100, 1 mM DTT, 1 mM EDTA, 20% glycerol, 0.5 mg/mL lysozyme, 10 mM MgCl$_2$, 15 ug/mL deoxyribonuclease I, and Complete TM protease inhibitor tablets (Roche). After addition of the lysis buffer, frozen cell pellets were resuspended using a tissue homogenizer. To reduce the viscosity of the sample, aliquots of the lysate were sonicated on ice using a microtip attached to a Branson sonicator. The sonicated lysate was centrifuged at 100,000×g for 30 minutes at 4° C. and filtered through a 0.2 μm filter unit (Corning).

The protein was purified using two sequential chromatography steps: Heparin sepharose CL-6B and polyU sepharose 4B. The chromatography buffers were identical to the lysis buffer but contained no lysozyme, deoxyribonuclease I, MgCl$_2$ or protease inhibitor and the NaCl concentration of the buffer was adjusted according to the requirements for charging the protein onto the column. Each column was eluted with a NaCl gradient which varied in length from 5-50 column volumes depending on the column type. After the final chromatography step, the resulting purity of the enzyme is >90% based on SDS-PAGE analysis. The enzyme was aliquoted and stored at −80° C.

HCV NS5B RdRp Enzyme Assay. An on-bead solid phase homogeneous assay was used in a 384-well format to assess NS5B inhibitors (Wang Y-K, Rigat K, Roberts S, and Gao M (2006) Anal Biochem, 359: 106-111). The biotinylated oligo dT$_{12}$ primer was captured on streptavidin-coupled imaging beads (GE, RPNQ0261) by mixing primer and beads in 1× buffer and incubating at room temperature for three hours. Unbound primer was removed after centrifugation. The primer-bound beads were resuspended in 3× reaction mix (20 mM Hepes buffer, pH 7.5, dT primer coupled beads, poly A template, $^3$H-UTP, and RNAse inhibitor (Promega N2515)). Compounds were serially diluted 1:3 in DMSO and aliquoted into assay plates. Equal volumes (10 μL) of water, 3× reaction mix, and enzyme in 3× assay buffer (60 mM Hepes buffer, pH 7.5, 7.5 mM MgCl$_2$, 7.5 mM KCl, 3 mM DTT, 0.03 mg/mL BSA, 6% glycerol) were added to the diluted compound on the assay plate. Final concentration of components in 384-well assay: 0.36 nM template, 15 nM primer, 0.29 μM ³H-UTP (0.3 µCi), 1.6 U/µL RNAse inhibitor, 7 nM NS5B enzyme, 0.01 mg/mL BSA, 1 mM DTT, and 0.33 µg/µL beads, 20 mM Hepes buffer, pH 7.5, 2.5 mM $MgCl_2$, 2.5 mM KCl, and 0.1% DMSO.

Reactions were allowed to proceed for 4 hours at 30° C. and terminated by the addition of 50 mM EDTA (10 µL). After incubating for at least 15 minutes, plates were read on an Amersham LEADseeker multimodality imaging system.

$IC_{50}$ values for compounds were determined using ten different [I]. $IC_{50}$ values were calculated from the inhibition using the four-parameter logistic formula $y=A+((B-A)/(1+((C/x)\hat{}D)))$, where A and B denote minimal and maximal % inhibition, respectively, C is the $IC_{50}$, D is hill slope and x represents compound concentration.

Cell Lines. The cell lines used to evaluate compounds consist of a human hepatocyte derived cell line (Huh-7) that constitutively expresses a genotype 1b HCV replicon containing a *Renilla* luciferase reporter gene. These cells were maintained in Dulbecco's modified Eagle medium (DMEM) containing 10% FBS, 100 U/mL penicillin/streptomycin and 1.0 mg/mL G418.

HCV Replicon Luciferase Assay. To evaluate compound efficacy, titrated compounds were transferred to sterile 384-well tissue culture treated plates, and the plates were seeded with HCV replicon cells (50 µL at a density of $2.4 \times 10^3$ cells/well) in DMEM containing 4% FBS (final DMSO concentration at 0.5%). After 3 days incubation at 37° C., cells were analyzed for *Renilla* Luciferase activity using the EnduRen substrate (Promega cat #E6485) according to the manufacturer's directions. Briefly, the EnduRen substrate was diluted in DMEM and then added to the plates to a final concentration of 7.5 µM. The plates were incubated for at least 1 h at 37° C. then read on a Viewlux Imager (PerkinElmer) using a luminescence program. The 50% effective concentration ($EC_{50}$) was calculated using the four-parameter logistic formula noted above.

To assess cytotoxicity of compounds, Cell Titer-Blue (Promega) was added to the EnduRen-containing plates and incubated for at least 4 hrs at 37° C. The fluorescence signal from each well was read using a Viewlux Imager. All $CC_{50}$ values were calculated using the four-parameter logistic formula.

Enzyme and replicon data for compound I is reported in Table 2.

TABLE 2

| Structure | $EC_{50}$, (µm) | $IC_{50}$ (µm) |
|---|---|---|
| Chiral 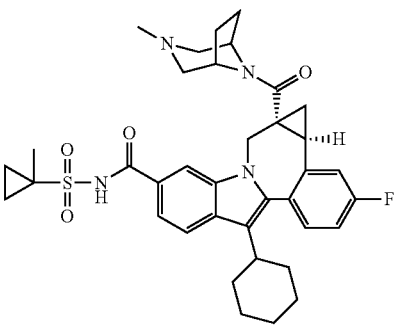 | 0.007 | 0.005 |

Compound I was evaluated for ion channel activity as determined by the following assays.

The ion channel responsible for the rapid component of the cardiac delayed rectifier potassium current (IKr) is encoded by the potassium channel gene, hERG (human ether-a-go-go-related gene). Mutations in hERG cause the chromosome 7-linked form of congenital long QT syndrome (LQT2). Prolongation of the QT interval and increased action potential duration (APD) can lead to the potentially fatal ventricular arrhythmia, torsade de pointes.

Method for Assessing hERG Potassium Channel with Flux. The hERG Flux assay is a relatively high throughput functional assay for predicting hERG inhibition which is FLIPR-based, and it has been validated against known IKr inhibitors and compared to patch-clamp, binding and in silico modeling data.

The hERG Flux assay was validated with clinical drugs that inhibit the hERG potassium channel and also prolong the cardiac QT interval. For 85% of compounds tested to date, the hERG Flux $IC_{50}$ data is right-shifted with respect to patch clamp $IC_{50}$ determinations by a median-fold difference of about seven, and the remaining 15% show greater than 10-fold shift. Accordingly, the hERG Flux data should be interpreted as follows: an $IC_{50}$ of <5 µM is considered potent with a high probability of having a sub-micromolar $IC_{50}$ in the hERG patch-clamp assay; 5-80 µM should be considered moderately potent, and >80 µM should be considered weak.

Cell Preparation. HEK293 cells stably-expressing hERG channels were grown in Dulbecco's Modified Eagle's Media supplemented with 10% Sigma fetal bovine serum, non-essential amino acids, 2 mM L-glutamine and 500 µg/mL G418, at 37° C. in a 5% $CO_2$ incubator. Cell are plated into 384-well Corning poly-D-lysine coated black/clear plates at a density of $2 \times 10^4$ cells per well (20 µl) in 10% serum media, and incubated for 15-24 hours at 37° C. in a 5% $CO_2$ incubator until a confluent monolayer of cells is obtained.

Loading of BTC Dye. A 2 mM stock of BTC-AM dye (Molecular Probes, Eugene, Oreg.) is prepared in 100% DMSO and then added 1:1 to 10% (w/v) pluronic acid in DMSO on the day of assay. The dye is then diluted in hERG external EP buffer. This BTC dye mixture (30 µl) is added to the cells and produces a final loading concentration of 2.5 µM. Cells are incubated at 21° C. for 45 minutes. The hERG external EP buffer contains 140 mM NaCl, 4.0 mM KCl, 1.8 mM $CaCl_2$, 1.0 mM $MgCl_2$, 10 mM HEPES, pH 7.3 and 10 mM glucose; this is the same buffer used for patch-clamp experiments (all buffer components obtained from Sigma Chemical).

Sample Preparation. Test samples are diluted to 10 mM DMSO and serially-diluted at a 1:2 ratio in DMSO in a 384-well plate. 2.5 µl serially-diluted test sample was transferred to 75 µl of hERG external electrophysiology (EP) buffer. After dye loading and buffer exchange, 10 µl of aqueous-diluted compounds are added to the cells of the two replicate plates. Compounds are pre-incubated with the cells for 30-45 minutes before the assay is read on the FLIPR. Sample preparation and the assay dilutions yield a ten-point final concentration range from 80 µM to 0.156 nM.

FLIPR Assay. Cells loaded with dye are read on the FLIPR384 (Molecular Devices, Sunnyvale, Calif.), which excites the dye using the 488 nm line of an argon laser.

Emission was filtered using a 540±30 nm bandpass filter. hERG channels are stimulated to open by the addition of 10 μl/well EP buffer containing 33 mM $K_2SO_4$ and 0.66 mM $Tl_2SO_4$ (Sigma/Aldrich). For each plate, data are collected every second for a period of 10 seconds, at which time the thallium-containing stimulus buffer is added. Data collection proceeds every second for 50 seconds, and then continues every three seconds for an additional 2 minutes. The addition of stimulus buffer produces a final volume of 50 μl at assay read, to give a final DMSO content of 0.65%.

Data Analysis. The statistical robustness of the hERG Flux assay is determined from blanks and totals wells. The totals wells (columns 21 and 22) define maximal hERG activation for each compound test plate (no test compound present), and the blanks wells (columns 23 and 24), which contain a saturating concentration of the hERG channel inhibitors (dofetilide or E-4031), define 100% hERG channel inhibition. The raw fluorescence units data files generated on the FLIPR plate reader are automatically exported and processed by in-house data analysis tools. The reduced percent inhibition data for each concentration of test compound were fit using MathIQ fitting engine (ID Business Solutions Limited, Surrey, UK). Data were analyzed by fitting maximum amplitudes of change in fluorescence, for thallium flux for a given condition of test compound. Potencies ($IC_{50}$ values) of compounds were calculated from the average of the two 10-point concentration response curves.

TABLE 3

FLIPR Data

| Structure | $IC_{50}$ (μM) |
|---|---|
| Chiral [structure] | 23.4 |

Method for Assessing hERG Potassium Channels with Patch Clamp.

Cell Line. Human embryonic kidney (HEK293) cells stably transfected with human ether-a-go-go related gene (hERG) cDNA were used in the hERG assay. The biophysical and pharmacological properties of recombinant hERG channels expressed in HEK293 cells and of native IKr channels in human cardiac cells are nearly identical. Several known hERG blockers, including dofetilide, terfenadine, cisapride and E-4031 inhibit recombinant hERG currents in the hERG stable cell line and IKr currents in isolated cardiac myocytes with identical potency.

Patch Clamp. Membrane current recordings were made with a Multiclamp 700 series integrating patch-clamp amplifier (Axon Instruments, Foster City, Calif.) using the whole-cell variant of the patch-clamp technique. Cells expressing hERG potassium channels were placed in a plexiglass bath chamber, mounted on the stage of an inverted microscope, and perfused continuously with bath solution.

The hERG bath solution, which replaced the cell culture media during experiments, contained (in mM): 140 NaCl, 4 KCl, 1.8 $CaCl_2$, 1 $MgCl_2$, 10 glucose, 10 HEPES (pH 7.4, NaOH). Borosilicate glass pipettes had tip resistances of 2 to 4 MΩ when filled with an internal solution containing (in mM): 130 KCl, 1 $MgCl_2$, 1 $CaCl_2$, 5 ATP-$K_2$, 10 EGTA, 10 HEPES (pH 7.2, KOH).

Initially, a current-voltage relationship was generated in the control bath solution using the following voltage protocol. hERG currents were elicited by 2 second step depolarizations applied from a holding potential of −80 mV to test potentials ranging from −70 mV to +60 mV. The voltage steps were applied in 20 second intervals. Tail currents were elicited upon repolarization to −65 mV for 3 seconds. While still perfusing with control bath solution, the voltage protocol was switched to one where repetitive test pulses (0.05 Hz) were applied from a holding potential of −80 mV to +20 mV for 2 seconds. Tail currents were elicited following the test pulses by stepping the voltage to −65 mV for 3 seconds. After recording the steady-state current for 2 to 5 minutes in the absence of test article (control), the bath solution was switched to one containing the lowest concentration of test article to be used. The peak tail current was monitored until a new steady-state in the presence of test article was achieved. This was followed by the application of the next higher concentration of test article to be tested, and was repeated until all concentrations of test article had been evaluated. Effects of test article on hERG channel were calculated by measuring inhibition of peak tail currents. Percent inhibition of tail currents was plotted as a function of test article concentration to quantify hERG channel inhibition. Test article effects were calculated using tail currents because there are no endogenous tail currents in plasmid-transfected control HEK293 cells. Membrane currents were sampled at rates at least 2 times the low pass filter rate. The flow rate was kept constant throughout the experiments. All currents were recorded at room temperature 25° C.

TABLE 4

Patch Clamp Data.

| Structure | Conc. (μM) | % Inhibition (Mean ± SE) | Replicates |
|---|---|---|---|
| Chiral [structure] | 10 | 30.5 ± 1.9 | 3 |

TABLE 4-continued

Patch Clamp Data.

| Structure | Conc. (μM) | % Inhibition (Mean ± SE) | Replicates |
|---|---|---|---|
| Chiral | 30 | 43.4 ± 2.0 | 3 |

What is claimed is:

1. The compound (1aR,12bS)-8-cyclohexyl-11-fluoro-N-((1-methylcyclopropyl)sulfonyl)-1a-((3-methyl-3,8-diazabicyclo[3.2.1]oct-8-yl)carbonyl)-1,1a,2,12b-tetrahydrocyclopropa[d]indolo[2,1-α][2]benzazepine-5-carboxamide (formula I) or a pharmaceutically acceptable salt thereof.

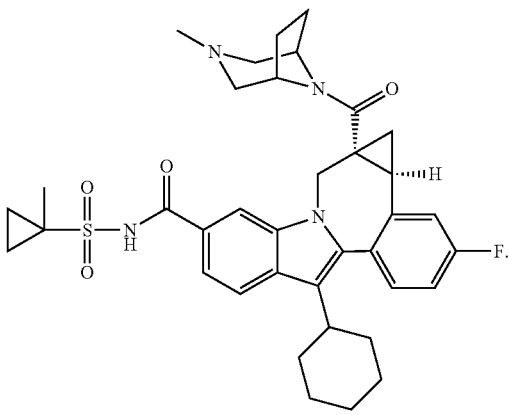

2. A pharmaceutical composition comprising a therapeutically effective amount of (1aR,12bS)-8-cyclohexyl-11-fluoro-N-((1-methylcyclopropyl)sulfonyl)-1a-((3-methyl-3,8-diazabicyclo[3.2.1]oct-8-yl)carbonyl)-1,1a,2,12b-tetrahydrocyclopropa[d]indolo[2,1-a][2]benzazepine-5-carboxamide or a pharmaceutically acceptable salt thereof, in association with a pharmaceutically acceptable adjuvant, carrier or diluent.

3. A method of treating hepatitis C infection comprising administering a therapeutically effective amount of a compound of claim 1 to a patient.

* * * * *

UNITED STATES PATENT AND TRADEMARK OFFICE
CERTIFICATE OF CORRECTION

PATENT NO. : 8,716,275 B2  
APPLICATION NO. : 13/651538  
DATED : May 6, 2014  
INVENTOR(S) : Zhizhen Barbara Zheng et al.

It is certified that error appears in the above-identified patent and that said Letters Patent is hereby corrected as shown below:

On the Title Page:

Item (71), Applicant, change "Bristol-Meyers Squibb Company" to -- Bristol-Myers Squibb Company --.

Item (57), ABSTRACT:
Column 2, line 2, change "((1 -methylcyclopropyl)" to -- ((1-methylcyclopropyl) --.

Column 2, line 3, change "oct-8-yl) carbonyl)-" to -- oct-8-yl)carbonyl)- --.

In the Specification:

Column 6, line 35, change "Imiqimod," to -- Imiquimod, --.
Column 6, line 36, change "5'-monophospate" to -- 5'-monophosphate --.
Column 7, line 23, change "Imiqimod," to -- Imiquimod, --.
Column 7, line 24, change "5'-monophospate" to -- 5'-monophosphate --.

In the Claims:

Claim 1:
Column 39, line 27, change "((1-methylcyclopropypl)" to -- ((1-methylcyclopropyl) --.
Column 39, line 29, change "[2,1-α]" to -- [2,1-a] --.
Column 39, line 30, change "thereof." to -- thereof, --.

Signed and Sealed this  
Seventh Day of April, 2015

Michelle K. Lee  
*Director of the United States Patent and Trademark Office*